United States Patent
Mochizuki

(10) Patent No.: US 11,083,950 B2
(45) Date of Patent: Aug. 10, 2021

(54) INFORMATION PROCESSING APPARATUS AND INFORMATION PROCESSING METHOD

(71) Applicant: SONY CORPORATION, Tokyo (JP)

(72) Inventor: Keita Mochizuki, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/307,062

(22) PCT Filed: Mar. 15, 2017

(86) PCT No.: PCT/JP2017/010517
§ 371 (c)(1),
(2) Date: Dec. 4, 2018

(87) PCT Pub. No.: WO2017/217050
PCT Pub. Date: Dec. 21, 2017

(65) Prior Publication Data
US 2019/0111327 A1   Apr. 18, 2019

(30) Foreign Application Priority Data
Jun. 16, 2016   (JP) .............................. JP2016-119688

(51) Int. Cl.
*A63B 69/36* (2006.01)
*G06F 3/01* (2006.01)
*A63B 69/00* (2006.01)
*G06T 13/40* (2011.01)
*G06T 7/00* (2017.01)
(Continued)

(52) U.S. Cl.
CPC .......... *A63B 69/3632* (2013.01); *A63B 69/00* (2013.01); *A63B 69/3608* (2013.01); *G06F 3/0346* (2013.01); *G06T 7/00* (2013.01); *G06T 13/40* (2013.01); *A63B 2220/803* (2013.01);
(Continued)

(58) Field of Classification Search
None
See application file for complete search history.

(56) References Cited

U.S. PATENT DOCUMENTS

2014/0066219 A1* 3/2014 Kim .................. G09B 19/0038
473/212
2015/0192413 A1   7/2015 Bellusci et al.

FOREIGN PATENT DOCUMENTS

EP          3063499 A2    9/2016
JP       2012-008862 A    1/2012
(Continued)

OTHER PUBLICATIONS

Liu et al. (Realtime Human Motion Control with a Small Number of Inertial Sensors, ACM, 2011) (Year: 2011).*
(Continued)

*Primary Examiner* — Kyle Zhai
(74) *Attorney, Agent, or Firm* — Chip Law Group

(57) ABSTRACT

An information processing apparatus including an acquisition section that acquires an operation model indicating an operation pattern related to a target object, a calculation section that calculates an overall operation including an identified partial operation of operations of the target object, with reference to the operation model acquired by the acquisition section, and an output control section that outputs information indicating the overall operation of the target object that has been calculated by the calculation section.

18 Claims, 14 Drawing Sheets

(51) Int. Cl.
　　　*G06F 3/0346*　　(2013.01)
　　　*G16H 20/30*　　(2018.01)
(52) U.S. Cl.
　　　CPC .............. *G06F 3/011* (2013.01); *G06F 3/017* (2013.01); *G16H 20/30* (2018.01)

(56) References Cited

FOREIGN PATENT DOCUMENTS

| JP | 2013-020578 A | 1/2013 |
|---|---|---|
| JP | 2016-010714 A | 1/2016 |
| WO | 2015/114468 A1 | 8/2015 |
| WO | 2015/114468 A2 | 8/2015 |

OTHER PUBLICATIONS

Chan et al. (A Virtual Reality Dance Training System Using Motion Capture Technology, vol. 4, No. 2, Apr.-Jun. 2011) (Year: 2011).*
Grosshauser et al. (Wearable Sensor Based Real-Time Sonification of Motion and Foot Pressure in Dance Teaching and Training, J. Audio Eng. Soc., vol. 1, No. 1, Oct. 2011) (Year: 2011).*
Ghasemzadeh et al. (Wearable coach for sport training: A quantitative model to evaluate wrist-rotation in golf, Journal of Ambient Intelligence and Smart Environments, 1 (2009)) (Year: 2009).*
Ghasemzadeh et al. (Energy-Efficient Information-Driven Coverage for Physical Movement Monitoring in Body Sensor Networks, IEEE, vol. 27, No. 1 Jan. 2009) (Year: 2009).*
Kawasaki, et al., "Generation of Character Animation Holding a Tool with Its Both Hands by Using Three 6DOF Trackers", IPSJ journal, vol. 45, No. 8, Aug. 2004, 2078-2086 pages.
Masaki Oshita, "Multi-Touch Interface for Character Motion Control Using Example-Based Posture Synthesis", 09 pages.
Masaki Oshita, et al., "Multi-Touch Interface for Character Motion Control Using Example-Based Posture Synthesis", 09 pages.
International Search Report and Written Opinion of PCT Application No. PCT/JP2017/010517, dated Jun. 6, 2017, 09 pages of ISRWO.
Masaki Oshita "Multi-Touch Interface for Character Motion Control Using Example-Based Posture Synthesis", 20th International Conference on Computer Graphics, Visualization and Computer Vision 2012, Jun. 2012, 213-222 pages.
Raita, et al.,"Generation of Character 1-16,18-20 Animation Holding a Tool with Its Both Hands by Using Three 6DOF Trackers", Transactions of Information Processing Society of Japan, 2004, vol. 45, No. 8.
Office Action for JP Patent Application No. 2018-523321, dated Mar. 2, 2021, 5 pages of Office Action and 4 pages of English Translation.
Masaki Oshita, "Multi-Touch Interface for Character Motion Control Using Example-Based Postyre Synthesis", 20th International Conference on Computer Graphics, Visuaization and Computer Vision, Jun. 2012, pp. 213-222.
Kawasaki et al., "Generation of Character Animation Holding a Tool with Its Both Hands by Using Three 6DOF Trackers", Human Body Animation Generation, Information Processing Society, vol. 45, No. 8, Aug. 2004, pp. 2078-2086.
Masaki Oshita, "Multi-Touch Interface for Character Motion Control Using Example-Based Posture Synthesis", 20th International Conference on Computer Graphics, Visualization and Computer Vision, XP055450396, Jun. 2012, pp. 213-222.
Kawasaki et al., "Generation of Character Animation Holding a Tool with Its Both Hands by Using Three 6DOF Trackers", Human Body Animation Generation, Information Processing Society, XP009510656, vol. 45, No. 8, Aug. 2004, pp. 2078-2086.
Mousas, et al., "Data-Driven Motion Reconstruction Using Local Regression Models", International Conference on Artificial Intelligence Applications and Innovations, XP055587234, vol. 436, Sep. 2014, pp. 364-374.
Liu, et al., "Realtime Human Motion Control with a Small Number of Inertial Sensors", Symposium on Interactive 3D Graphics and Games, San Francisco, CA, USA, XP055587236, Feb. 18-20, 2011, pp. 133-140.
Eom, et al., "Data-Driven Reconstruction of Human Locomotion Using a Single Smartphone", Pacific Graphics 2014, XP055587251, vol. 33, No. 7, Oct. 28, 2014, pp. 11-19.
Yu, et al., "Potential of IMU Sensors in Performance Analysis of Professional Alpine Skiers", MDPI, Sensors, XP055792018, vol. 16, No. 4, Apr. 1, 2016, 21 pages.
Office Action for EP Patent Application No. 17812956.5, dated Apr. 9, 2021, 8 pages of Office Action.

\* cited by examiner

INFORMATION PROCESSING APPARATUS AND INFORMATION PROCESSING METHOD

CROSS REFERENCE TO RELATED APPLICATIONS

This application is a U.S. National Phase of International Patent Application No. PCT/JP2017/010517 filed on Mar. 15 2017, which claims priority benefit of Japanese Patent Application No. JP 2016-119688 filed in the Japan Patent Office on Jun. 16, 2016. Each of the above-referenced applications is hereby incorporated herein by reference in its entirety.

TECHNICAL FIELD

The present disclosure relates to an information processing apparatus, an information processing method, and a storage medium.

BACKGROUND ART

Recently, technology to visualize (that is, to digitize) a move of a body has been actively developed. In the field of sports, for example, technology is being developed to attach sensor devices to various parts of a body for visualizing a move of the body on the basis of the measurement results and contributing to improvement in forms, and the like.

For example, Patent Literature 1 described below discloses a technology of appropriately setting an analysis section of output data obtained from a sensor device mounted on a user or a tool used by a user, for enhancing determination accuracy of a motion pattern such as a serve and a smash in tennis.

CITATION LIST

Patent Literature

Patent Literature 1: JP 2016-10714A

DISCLOSURE OF INVENTION

Technical Problem

Nevertheless, it is hard to say that the technology proposed in Patent Literature 1 described above is sufficient as a technology to visualize an operation of a target object. For example, one aspect of the insufficiency lies on the reduction of an information amount required for visualizing the operation of the target object. In view of the foregoing, a mechanism that can visualize an operation of a target object from a smaller amount of information is desirably provided.

Solution to Problem

According to the present disclosure, there is provided an information processing apparatus including: an acquisition section configured to acquire an operation model indicating an operation pattern related to a target object; a calculation section configured to calculate an overall operation including an identified partial operation of operations of the target object, with reference to the operation model acquired by the acquisition section; and an output control section configured to output output information indicating the overall operation of the target object that has been calculated by the calculation section.

In addition, according to the present disclosure, there is provided an information processing method including: acquiring an operation model indicating an operation pattern related to a target object; calculating, by a processor, an overall operation including an identified partial operation of operations of the target object, with reference to the acquired operation model; and outputting output information indicating the calculated overall operation of the target object.

In addition, according to the present disclosure, there is provided a storage medium storing a program for causing a computer to function as: an acquisition section configured to acquire an operation model indicating an operation pattern related to a target object; a calculation section configured to calculate an overall operation including an identified partial operation of operations of the target object, with reference to the operation model acquired by the acquisition section; and an output control section configured to output output information indicating the overall operation of the target object that has been calculated by the calculation section.

Advantageous Effects of Invention

As described above, according to the present disclosure, a mechanism that can visualize an operation of a target object from a smaller amount of information is provided. Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
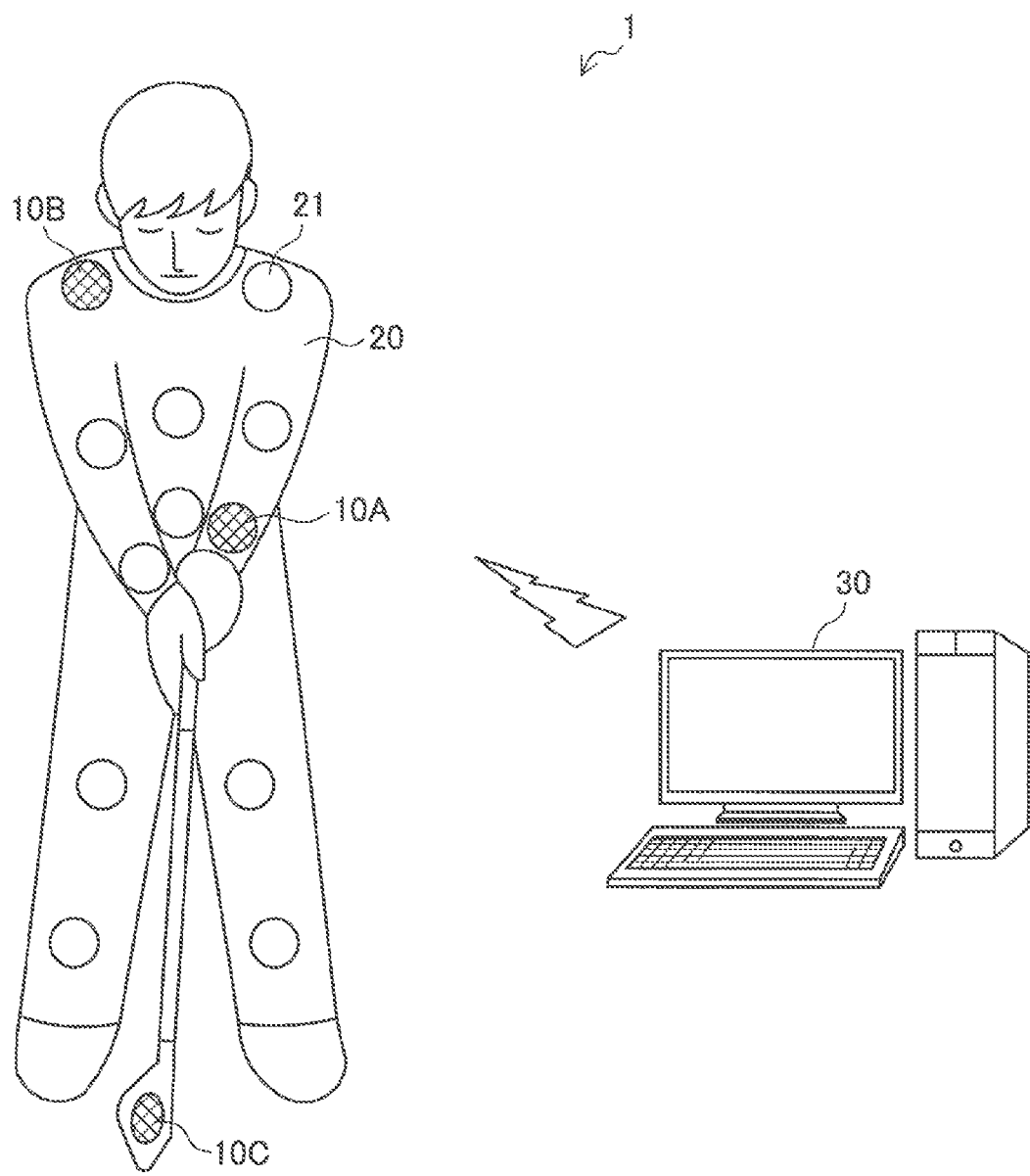
FIG. 1 is a diagram for describing an outline of a system according to a first embodiment.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

In addition, in the specification and the drawings, different alphabetical letters may be given to components having substantially the same functional configuration for distinction after the same symbol is given to the components. For example, a plurality of components having substantially the same functional configuration are distinguished as sensor devices 10A, 10B, and 10C as necessary. However, in a case where it is unnecessary to particularly distinguish each of the plurality of components having substantially the same functional configuration, only the same symbol is given. For example, in a case where it is unnecessary to particularly distinguish sensor devices 10A, 10B, and 10C, the sensor devices are simply referred to as a sensor device 10.

Note that the description will be given in the following order.

1. First Embodiment
1.1. Outline of system
1.2. Configuration example of sensor device
1.3. Configuration example of information processing apparatus
1.4. Technical feature
1.5. Flow of processing
2. Second Embodiment
2.1. Configuration example of information processing apparatus
2.2. Technical feature
2.3. Flow of processing
3. Hardware configuration example
4. Conclusion

1. First Embodiment

The present embodiment is a mode of visualizing an operation of a real object.

<1.1. Outline of System>

FIG. 1 is a diagram for describing an outline of a system 1 according to the present embodiment. As illustrated in FIG. 1, the system 1 includes a plurality of sensor devices 10 (that is, 10A to 10C) attached to a sensor attachment apparatus 20.

The sensor device 10 is a device that measures various kinds of data. The sensor device 10 is attached to a sensor attachment tool 21 included in the sensor attachment apparatus 20 to perform measuring targeting a move of a target object. A target object may be a human, a dog, a cat, or other living organisms, or may be a non-living organism such as a robot. In the example illustrated in FIG. 1, a target object is a user (that is, a human). In addition, the target object may be an object to be used by a living organism. For example, the target object may be a tool to be used for games such as a golf club, a tennis racket, a ski board, a ski boot, a goal, or a bat. In addition, the target object may be a tool to be used for living such as an artificial hand or a wheelchair. In addition, the target object may be a tool to be used for animals such as a collar or a horseshoe.

The sensor device 10 transmits information indicating a measurement result (hereinafter, also referred to as sensor information), to an information processing apparatus 30. The transmission may be performed in real time concurrently with the measurement, or the information may be stored and transmitted at an arbitrary timing after the measurement.

The sensor attachment apparatus 20 is an apparatus for fixing the sensor device 10 to a target object. As illustrated in FIG. 1, the sensor attachment apparatus 20 has one or more attachment positions (the sensor attachment tool 21) for removably attaching the sensor devices 10, and the sensor devices 10 can be attached to a part of or all of the attachment positions. The sensor attachment apparatus 20 may be formed into a shape that covers a part of or all of the trunk, the limbs, or the like of a user, and in that case, it is desirable to form the sensor attachment apparatus 20 with extendable and retractable materials so that a move of a user is not disturbed. In addition, the attached sensor device 10 may be separated from the target object, and the sensor attachment apparatus 20 may have thickness like a helmet, a protector, and the like do. Additionally, the sensor attachment apparatus 20 may be attached to or be integrally formed with an object such as a golf club, a tennis racket, and a ski board. A user can attach the sensor device 10 to the sensor attachment tool 21 positioned in a region that the user wants to measure.

The information processing apparatus 30 acquires the sensor information from the sensor device 10, and performs various kinds of processing for visualizing an operation of a target object.

<1.2. Configuration Example of Sensor Device>

Figure 2:
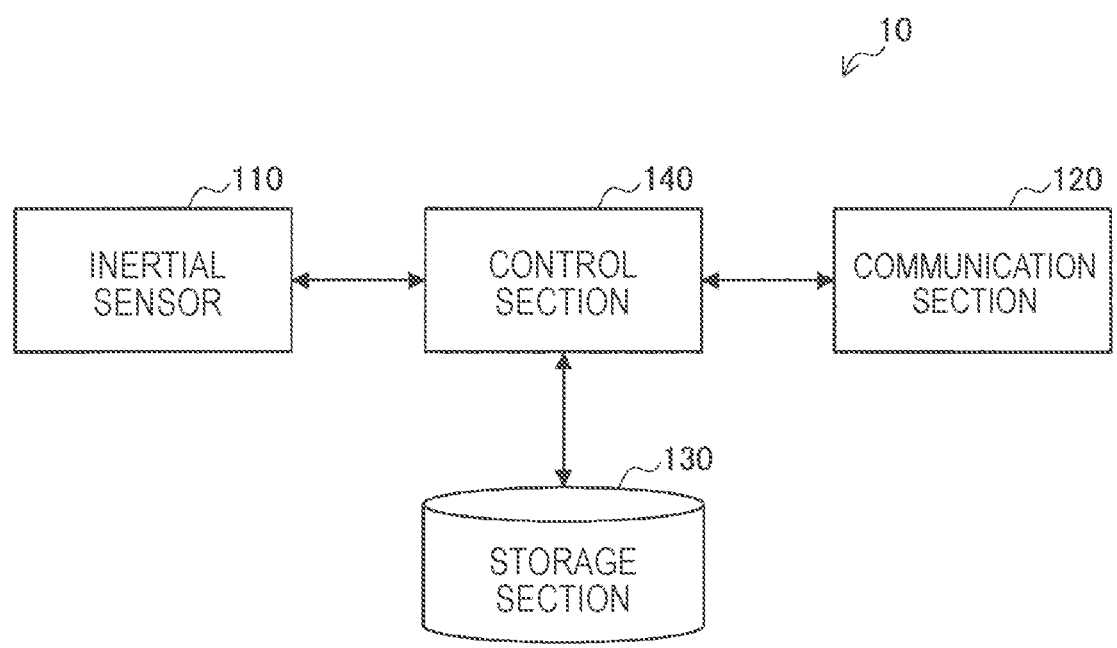
FIG. 2 is a block diagram illustrating an example of a configuration of a sensor device according to the embodiment.

FIG. 2 is a block diagram illustrating an example of a configuration of the sensor device 10 according to the present embodiment. As illustrated in FIG. 2, the sensor device 10 according to the present embodiment includes an inertial sensor 110, a communication section 120, a storage section 130, and a control section 140.

(1) Inertial Sensor 110

The inertial sensor 110 is a device that performs measurement using inertia. The inertial sensor 110 includes an acceleration sensor, a gyro sensor, a geomagnetic sensor, and the like, and outputs the measured sensor information (e.g. acceleration and angular speed) to the control section 140.

(2) Communication Section 120

The communication section 120 is a communication module for performing transmission and reception of data between itself and the information processing apparatus 30 in a wired/wireless manner. The communication section 120 can perform communication conforming to an arbitrary communication method such as a Local Area Network (LAN), a wireless LAN, Wi-Fi (registered trademark), Bluetooth (registered trademark), or infrared communication, for example. The communication section 120 transmits the sensor information measured by the inertial sensor 110, to the information processing apparatus 30.

(3) Storage Section 130

The storage section 130 temporarily or permanently stores programs and various types of data for operations of the sensor device 10. For example, the storage section 130 temporarily stores the information measured by the inertial sensor 110.

(4) Control Section 140

The control section 140 corresponds to a Central Processing Unit (CPU), a Digital Signal Processor (DSP), or the like, and performs processing for providing various types of functions of the sensor device 10. The sensor device 10 operates on the basis of control performed by the control section 140. The operation of the sensor device 10 that is based on the control performed by the control section 140 will be described in detail later.

<1.3. Configuration Example of Information Processing Apparatus>

Figure 3:
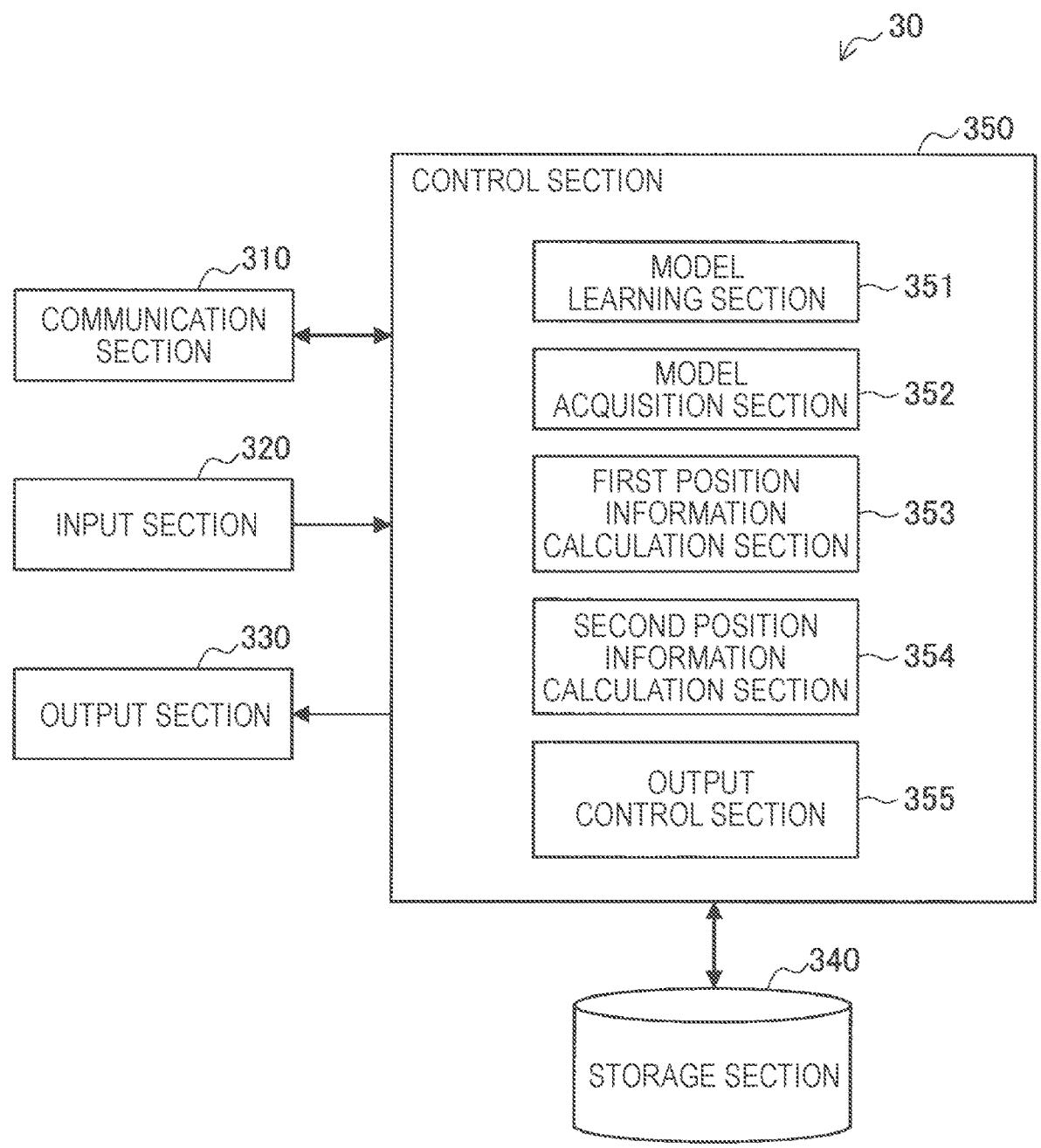
FIG. 3 is a block diagram illustrating an example of a configuration of an information processing apparatus according to the embodiment.

FIG. 3 is a block diagram illustrating an example of a configuration of the information processing apparatus 30 according to the present embodiment. As illustrated in FIG. 3, the information processing apparatus 30 according to the present embodiment includes a communication section 310, an input section 320, an output section 330, a storage section 340, and a control section 350.

(1) Communication Section 310

The communication section 310 is a communication module for performing transmission and reception of data between itself and the sensor device 10 in a wired/wireless manner. The communication section 310 can perform communication conforming to an arbitrary communication method such as a LAN, a wireless LAN, Wi-Fi, Bluetooth, or infrared communication, for example. The communication section 310 receives the sensor information from the sensor device 10.

(2) Input Section 320

The input section 320 receives an input of information. For example, the input section 320 receives an input of information from the user. The input section 320 outputs the input information to the control section 350.

(3) Output Section 330

The output section 330 performs an output of information. For example, the output section 330 outputs information using an image, a sound, vibration, and/or the like. The output section 330 outputs information on the basis of control performed by the control section 350.

(4) Storage Section 340

The storage section 340 temporarily or permanently stores programs and various types of data for operations of the information processing apparatus 30. For example, the storage section 340 stores an operation model to be described later.

(5) Control Section 350

The control section 350 corresponds to a CPU, a DSP, or the like, and performs processing for providing various types of functions of the information processing apparatus 30. The control section 350 may be regarded as at least one electrical circuit formed so as to be able to execute functional units disclosed in FIG. 3. As illustrated in FIG. 3, the control section 350 includes a model learning section 351, a model acquisition section 352, a first position information calculation section 353, a second position information calculation section 354, and an output control section 355. Note that the control section 350 can further include structural elements other than these structural elements. In other words, the control section 350 can also perform operations other than operations of these structural elements. The operations of these structural elements will be described in detail later.

<1.4. Technical Feature>

(1) Target Object

In the present embodiment, a target object is a real object. In addition, position information in the present embodiment is a three-dimensional coordinate (i.e. X-coordinate, Y-coordinate, and Z-coordinate) in a real space.

For example, the target object includes one or more moving objects. In other words, the target object may be singular or plural. For example, a human and an object (e.g. tool) manipulated by a human can be the target object. The operation of the target object is represented by a time series variation of the attitude of the target object.

For example, the target object may include a moving object having a plurality of joints. Examples of such a target object include a human, a robot, and the like. In addition, the operation of the target object may include time series variations of position information pieces of the plurality of joints of the moving object. In other words, the information processing apparatus 30 can visualize a complicated operation in which a positional relationship between the joints varies.

In the present embodiment, a target object to be visualized is assumed to be a human. Hereinafter, a human serving as a target object will also be referred to as a user.

The sensor device 10 is arranged in an arbitrary region of the target object. For example, the sensor device 10 may be arranged at a joint of the user. In this case, the sensor attachment tool 21 is arranged at the joint of the user. A region in which the sensor device 10 is to be arranged, such as a position of the sensor attachment tool 21 to which the sensor device 10 is to be attached, for example, will also be referred to as a first point. On the other hand, a region in which the sensor device 10 is not arranged, such as a position of the sensor attachment tool 21 to which the sensor device 10 is not attached, for example, will also be referred to as a second point.

A manipulator of the information processing apparatus 30 and the user may be the same person, or may be different persons. As an example, the following description will be given assuming that the manipulator and the user are the same person.

(2) Calculation of Position Information that is Based on Sensor Information

On the basis of sensor information measured by one or more sensor devices 10 arranged on the target object, the information processing apparatus 30 (e.g. the first position information calculation section 353) identifies a time series variation of position information of the one or more sensor devices 10. More briefly, the information processing apparatus 30 calculates position information of the first point on the basis of the sensor information. For example, the information processing apparatus 30 calculates the position information of the first point from the sensor information acquired from the sensor device 10, using an inertial navigation system (INS).

The inertial navigation system is a technology of calculating a sensor position by integrating angular speed and acceleration a plurality of times, and is employed in ships, airplanes, or the like, for example. In the inertial navigation system, first of all, by integrating angular speed (performing first integration), an attitude (i.e. an attitude angle in the real space) of a sensor device is calculated. Subsequently, by integrating acceleration (performing second integration), speed of the sensor device is calculated. Next, by integrating speed (performing third integration), a moving distance of the sensor device is calculated. Then, by combining vectors of moving distances and attitudes (i.e. moving directions) for each subdivision point, relative position information starting from an initial position is calculated. If the initial position is already known, absolute position information (i.e. a three-dimensional coordinate in the real space) of the sensor device can be calculated by the above calculation.

For example, an example of measuring a state in which the user swings a golf club called an iron will be assumed. As an example, the sensor devices 10 are assumed to be attached to a neck, an waist, a right knee, a right foot, a left knee, a left foot, a hand, and a club head of the iron. In this case, the information processing apparatus 30 can visualize an operation in which the user swings the iron, by calculating position information of each of the sensor devices 10. The example of the visualization will be described with reference to FIG. 4.

Figure 4:
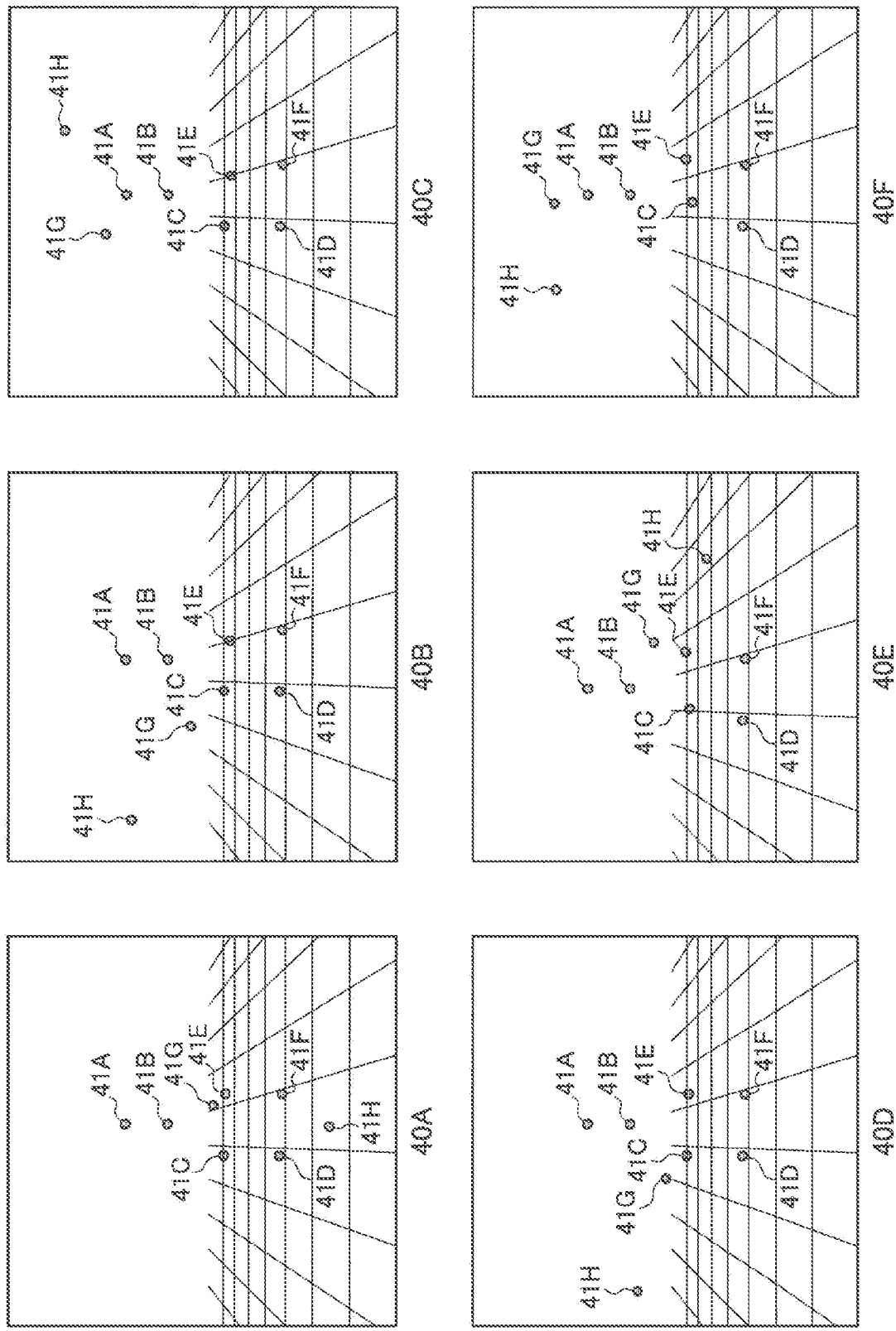
FIG. 4 is a diagram illustrating an example of visualization processing of a user operation according to the embodiment.

FIG. 4 is a diagram illustrating an example of visualization processing of a user operation according to the present embodiment. Attitudes 40A to 40F indicate attitudes (i.e. position information pieces of the respective sensor devices 10) at the respective timings of the user that swings the iron, and time flows in order from the attitude 40A toward the attitude 40F. The attitude 40A indicates an attitude at a timing at which the user holds the iron at the ready. The attitude 40B indicates an attitude at a timing of a back swing. The attitude 40C indicates an attitude at a timing at which the back swing has reached the top. The attitude 40D indicates an attitude at a timing of a down swing. The attitude 40E indicates an attitude at a timing of follow through. The attitude 40F indicates an attitude at a timing of finish. Plots 41 in each attitude indicate positions to which the sensor devices 10 are attached. A plot 41A corresponds to a neck, a plot 41B corresponds to an waist, a plot 41C corresponds to a right knee, a plot 41D corresponds to a right foot, a plot 41E corresponds to a left knee, a plot 41F corresponds to a left foot, a plot 41G corresponds to a hand, and a plot 41H corresponds to a club head of the iron.

Aside from the inertial navigation system, the information processing apparatus 30 can calculate the position information of the first point using an arbitrary algorithm. For example, by an optical motion capture technology that uses a captured image of a marker provided on a partial joint of the user, the information processing apparatus 30 may calculate position information of the joint to which the marker is added.

(3) Operation Model

An operation model is information indicating an operation pattern of a modeled object related to a target object.

The modeled object is an object to which the sensor device 10 is attached. The target object and the modeled object may be the same, or may be different. For example, the user and a person modeled as a modeled object may be the same person, or may be different persons.

The operation model differs depending on the context, and is stored in the storage section 340 for each context. In other words, the operation model can include a plurality of operation models corresponding to contexts, such as a first operation model corresponding to a first context, and a second operation model corresponding to a second context. The operation model is information indicating a time series variation of position information of each region of a modeled object that is obtainable in a case where the information processing apparatus 30 operates in a context in which there is a modeled object. As an example, an operation model related to a swing operation of the iron will be described. In this case, the operation model includes information indicating time series variations of position information pieces of the respective regions of the neck, the waist, the right knee, the right foot, the left knee, the left foot, the hand, and the club head of the iron, for example. Here, the respective regions corresponding to the position information pieces included in the operation model correspond to regions in which the sensor devices 10 are arranged (i.e. positions in which the sensor attachment tool 21 are arranged).

Various types of contexts can be considered. For example, the contexts can include the type of the modeled object, the type of an operation performed by the modeled object, attribute information of the modeled object, and information indicating a state. Specifically, for example, in a case where the modeled object is a person, the contexts can include the type of an operation such as walking, running, golf, and tennis, attribute information such as gender, age, a body height, and a body weight, information indicating a health state, a habit of an operation, etc., and the like.

For example, the operation model can be represented as a regression model. In addition, the operation model may be represented in a format obtained by dimension-compressing multidimensional information.

In addition, the information processing apparatus 30 (the model learning section 351) may learn an operation model. For example, as for a swing operation of the iron, the information processing apparatus 30 generates an operation model on the basis of calculation of position information that is based on sensor information obtainable in a case where the user performs a swing operation in a state in which the sensor devices 10 are attached to all the sensor attachment tools 21 and the club head of the iron.

(4) Selection of Operation Model

The information processing apparatus 30 (e.g. the model acquisition section 352) acquires at least one operation model related to a target object. Specifically, the information processing apparatus 30 acquires, from among operation models stored in the storage section 340, an operation model corresponding to the context of the target object. For example, as for a swing operation of the iron, the information processing apparatus 30 acquires an operation model in which a modeled object is a person, and the type of an operation is golf.

For example, the information processing apparatus 30 may acquire an operation model on the basis of a user manipulation. For example, the context of the user is input to the information processing apparatus 30 by the user itself, and an operation model corresponding to the input context is selected. In this case, it becomes possible to correctly refer to an operation model corresponding to the context designated by the user. Note that the user manipulation includes both of an intentionally-performed manipulation (e.g. manual manipulation) and an unconsciously-performed manipulation (e.g. image recognition of an operation).

For example, the information processing apparatus 30 may acquire an operation model corresponding to an identified partial operation of operations of the target object. Therefore, first of all, the information processing apparatus 30 recognizes a context on the basis of a partial operation of the user that has been identified using the sensor information measured by the sensor device 10 arranged on the user. In other words, the information processing apparatus 30 recognizes a context of the user on the basis of the time series variation of the calculated position information of the first point. Subsequently, the information processing apparatus 30 automatically acquires, from the storage section 340, an operation model corresponding to the recognized context.

For example, the information processing apparatus 30 automatically acquires one of the first operation model and the second operation model in accordance with the recognized context. In this case, it becomes possible for the information processing apparatus 30 to reduce the burden of a context input.

Note that the information processing apparatus 30 may acquire the first operation model and the second operation model at different timings. In this case, the information processing apparatus 30 can change an operation model to be referred to, in accordance with a change in the context of the user. In addition, the information processing apparatus 30 may simultaneously acquire the first operation model and the second operation model. In this case, it becomes possible for the information processing apparatus 30 to calculate an operation of the target object by combining a plurality of operation models.

(5) Calculation of Position Information that is Based on Operation Model

The information processing apparatus 30 (e.g. the second position information calculation section 354) calculates an overall operation including the identified partial operation of the operations of the target object, with reference to the acquired operation model. Because the information processing apparatus 30 can calculate the overall operation even in a case where only a part of the operations of the target object is identified, the operation of the target object can be visualized from a smaller amount of information. Note that, as the number of first points increases, the accuracy of visualization is enhanced.

More specifically, the information processing apparatus 30 calculates a time series variation of position information of another region of the target object that follows an operation pattern indicated by an operation model, and corresponds to a time series variation of position information of one or more sensor devices. In other words, the information processing apparatus 30 calculates a time series variation of position information of the second point that follows an operation pattern indicated by an operation model, and corresponds to a time series variation of position information of the first point. It thereby becomes possible for the information processing apparatus 30 to calculate an overall operation of the user that includes time series variations of the position information of the first point and the position information of the second point. Note that, hereinafter, calculating the position information of the second point will also be referred to as predicting.

For example, the information processing apparatus 30 may calculate an overall operation on the basis of an identified partial operation of the operations of the user, with reference to an operation model. The target object may be a plurality of objects, and the information processing apparatus 30 may calculate operations of the objects manipulated by the user, on the basis of a part or all of operations of the user that have been identified, with reference to an operation model. For example, the information processing apparatus 30 calculates an operation of a golf club swung by the user, on the basis of an identified swing operation of the user, with reference to an operation model related to a swing operation of a golf club. It thereby becomes possible to calculate the trajectory of the golf club even if the sensor device 10 is not attached to the golf club.

The following assumption will be given of an example of measuring a state in which the user swings an iron, similarly to the example illustrated in FIG. 4. Nevertheless, unlike the example illustrated in FIG. 4, the sensor devices 10 are assumed to be attached only to the right knee and the hand.

The example of the visualization will be described with reference to FIG. 5 and FIG. 6.

Figure 5:
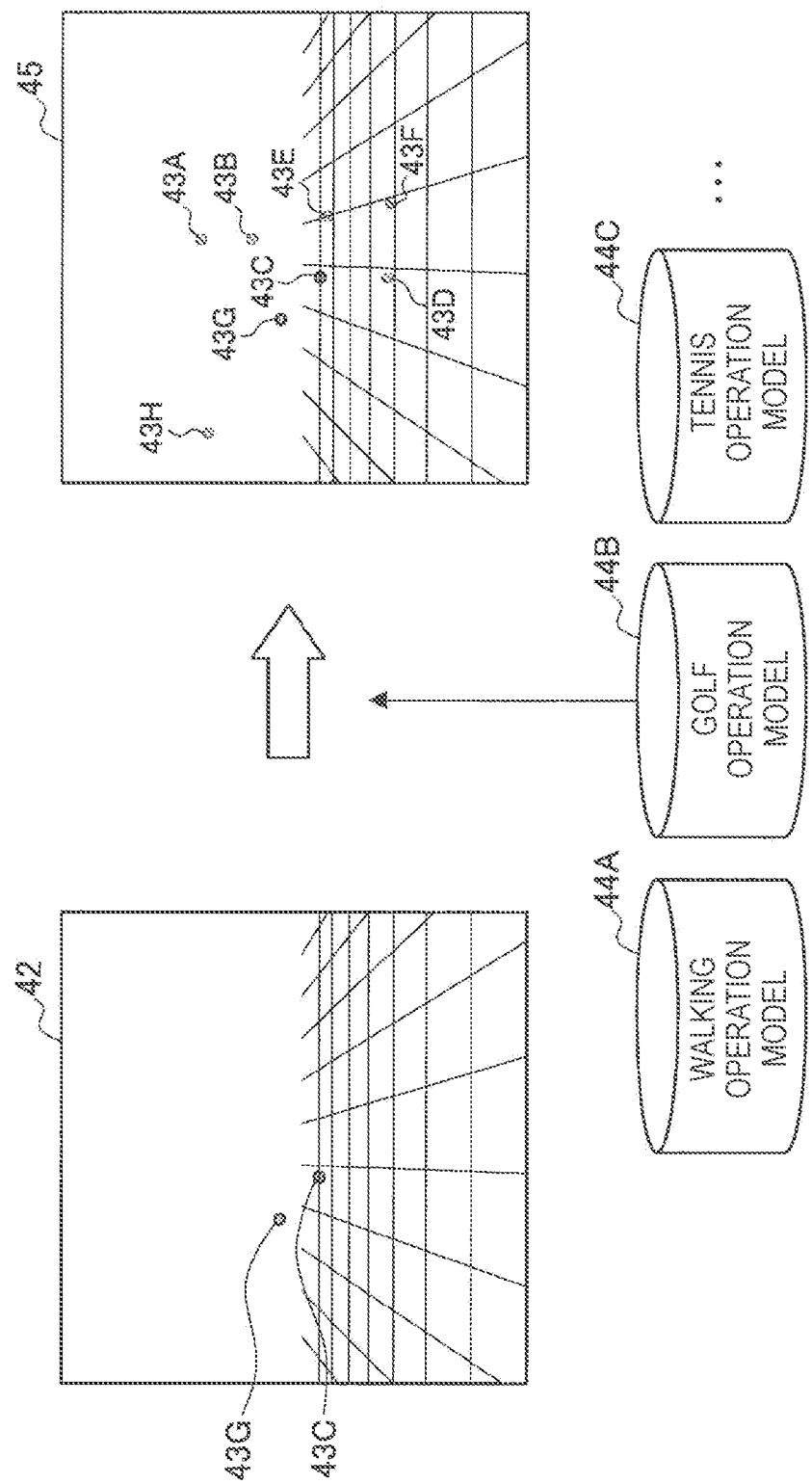
FIG. 5 is a diagram illustrating an example of visualization processing of a user operation according to the embodiment.

FIG. 5 is a diagram illustrating an example of visualization processing of a user operation according to the present embodiment. First of all, the information processing apparatus 30 (e.g. the first position information calculation section 353) calculates position information pieces of first points (i.e. the right knee and the hand) to which the sensor devices 10 are attached. An attitude 42 indicates a part of attitudes of the user that is measured at a timing of a back swing, and a plot 43C corresponds to the right knee and a plot 43G corresponds to the hand. Subsequently, the information processing apparatus 30 (e.g. the model acquisition section 352) selects, as an operation model corresponding to a context of the user, a golf operation model 44B from among a walking operation model 44A, the golf operation model 44B, and a tennis operation model 44C. Then, the information processing apparatus 30 (e.g. the second position information calculation section 354) predicts position information pieces of second points (i.e. the neck, the waist, the right foot, the left knee, the left foot, and the club head of the iron), from the position information pieces of the first points, with reference to the golf operation model 44B. An attitude 45 indicates an attitude obtained by adding prediction results of other attitudes to the part of the attitudes of the user that is measured at the timing of the back swing. A plot 43A indicates the neck, a plot 43B indicates the waist, a plot 43D indicates the right foot, a plot 43E indicates the left knee, a plot 43F indicates the left foot, and a plot 43H indicates the club head of the iron.

Figure 6:
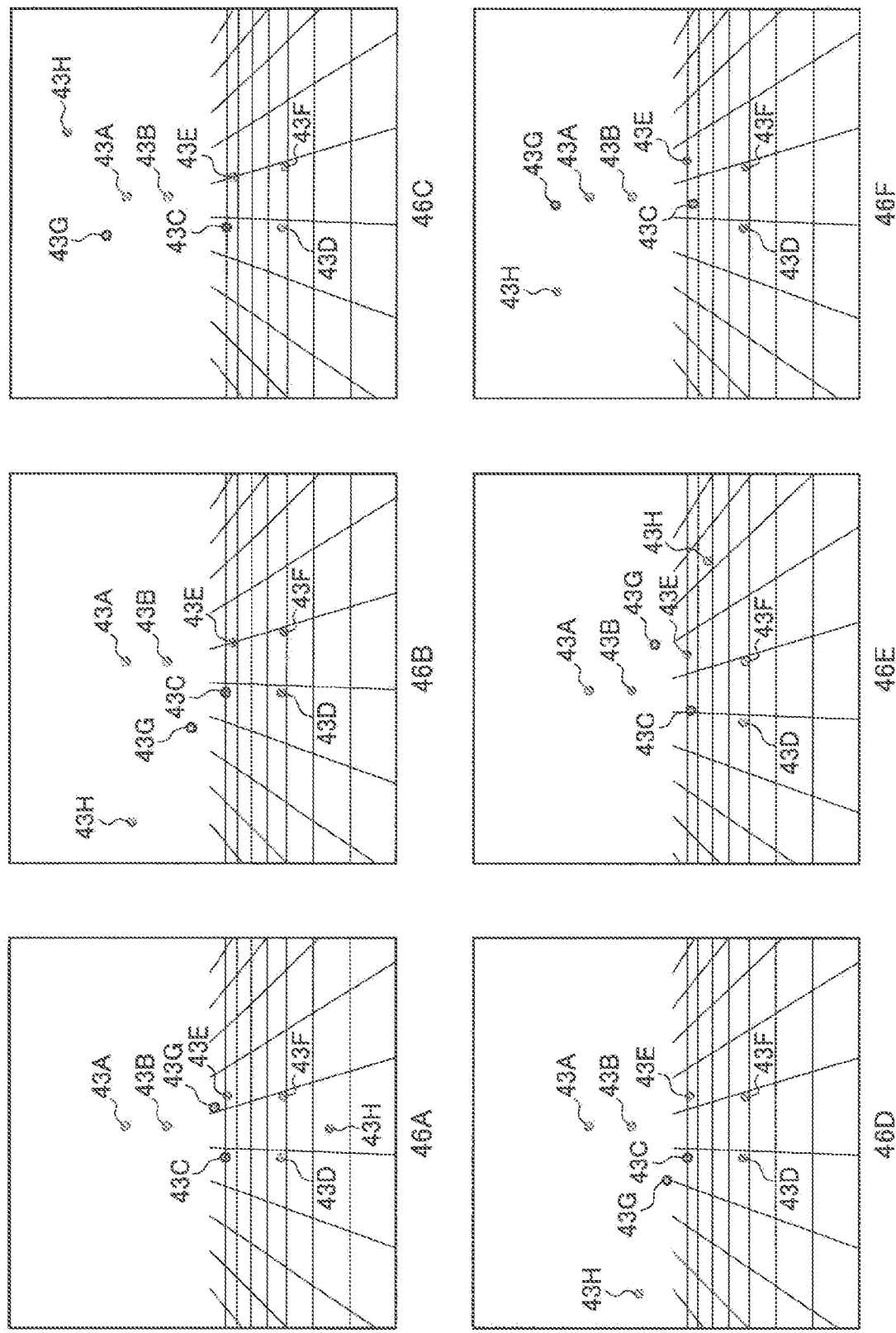
FIG. 6 is a diagram illustrating an example of visualization processing of a user operation according to the embodiment.

By performing the above-described prediction processing at each timing of the swing, the information processing apparatus 30 can visualize the entire operation in which the user swings the iron, as illustrated in FIG. 6.

FIG. 6 is a diagram illustrating an example of visualization processing of a user operation according to the present embodiment. Attitudes 46A to 46F indicate positions (plots 43C and 43G) of the sensor devices 10, and prediction results (plots 43A, 43B, 43D, 43E, 43F, and 43H) of positions of the other regions, at the respective timings of the user that performs a swing operation. Time flows in order from the attitude 46A toward the attitude 46F, and the timings from the attitude 46A to the attitude 46F are similar to the respective timings from the attitude 40A to the attitude 40F in FIG. 4. In addition, the attitude 45 illustrated in FIG. 5 corresponds to the attitude 46B in FIG. 6.

In this manner, by predicting position information pieces of the regions to which the sensor devices 10 are not attached, from the position information pieces of the sensor devices 10, the information processing apparatus 30 can visualize the entire swing operation of the user.

Here, it is desirable that the sensor device 10 is arranged at a joint corresponding to a context, among a plurality of predefined joints. This is because the arrangement position that can assure prediction accuracy can vary depending on the context. More specifically, as described later, it is desirable that the sensor device 10 is arranged at a joint corresponding to a factor having a large factor loading that is indicated by a principal component result in each context. For example, in a case where a context is a swing operation of a golf club, it is desirable that the sensor devices 10 are arranged at two locations including the hand and the knee (the right knee in the case of right handedness). It thereby becomes possible to predict a swing operation using a smaller number of sensor devices 10.

(6) Prediction Algorithm

Various types of prediction algorithms of position information pieces of second points can be considered.

Linear Regression

For example, using a linear regression model, the information processing apparatus 30 (e.g. the second position information calculation section 354) may predict position information pieces of second points by treating position information pieces of first points as inputs. In this case, an operation model is the linear regression model.

Figure 7:
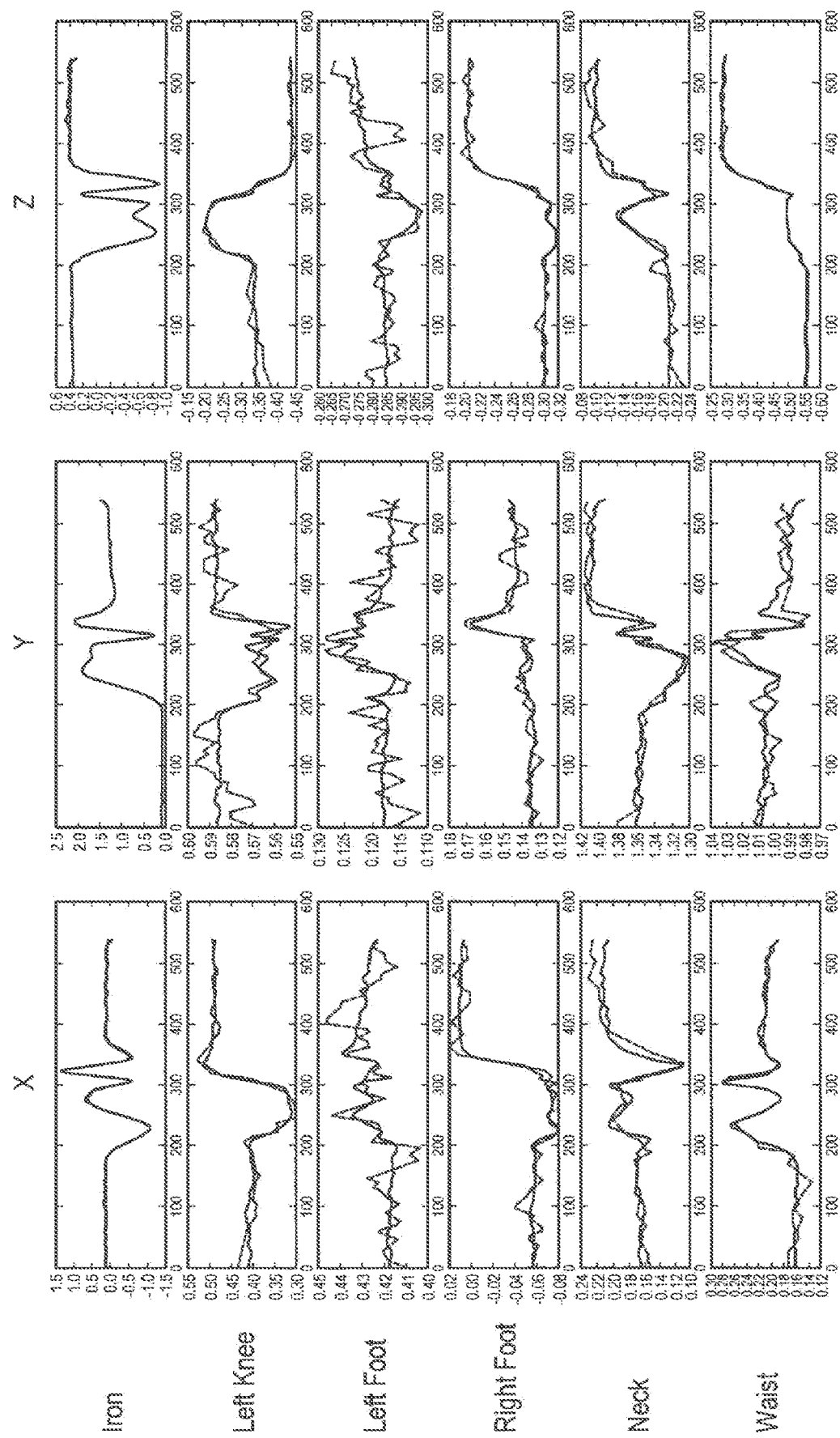
FIG. 7 is a diagram for describing an example of a prediction algorithm according to the embodiment.

FIG. 7 is a diagram for describing an example of a prediction algorithm according to the present embodiment. FIG. 7 represents time series variations of position information pieces of the iron, the left knee, the left foot, the right foot, the neck, and the waist that are to be obtained in a case where position information pieces of the right knee and the hand are input to the regression model. A horizontal axis of each graph illustrated in FIG. 7 indicates a time, and a vertical axis indicates an X-coordinate, a Y-coordinate, or a Z-coordinate. In addition, a broken line in each graph indicates a time series variation of position information at the time of learning, and a solid line indicates a time series variation of position information at the time of prediction.

Note that, in a case where the linear regression model is constructed as a probability model, the information processing apparatus 30 may predict position information pieces of second points by the Bayes' estimation. The method of linear regression is not limited to the Bayes' estimation, and various kinds of models can be used.

Dimension Compression

For example, the information processing apparatus 30 (e.g. the second position information calculation section 354) may predict position information pieces of second points using a dimension-compressed operation model.

For example, the above-described swing operation of the iron is represented by three pieces of information including an X-coordinate, a Y-coordinate, and a Z-coordinate of each of eight regions including the neck, the waist, the right knee, the right foot, the left knee, the left foot, the hand, and the club head of the iron, that is to say, represented by 24-dimensional information in total. The dimension-compressed operation model represents the 24-dimensional information as information in the dimension having a dimension number smaller than 24. For example, Principal Component Analysis (PCA) can be used for dimension compression.

Because there is a strong high-speed condition for the attitude of a person, it is generally known that a multidimensional space represented by attitude parameters (i.e. position information pieces of the respective joints) having a multi-degree of freedom can be represented in a lower-dimensional space. Treating the attitude of a person in a low-dimensional space can be said to be equal to subconsciously considering a skeleton model.

An example of the dimension-compressed operation model will be described below with reference to FIG. 8.

Figure 8:
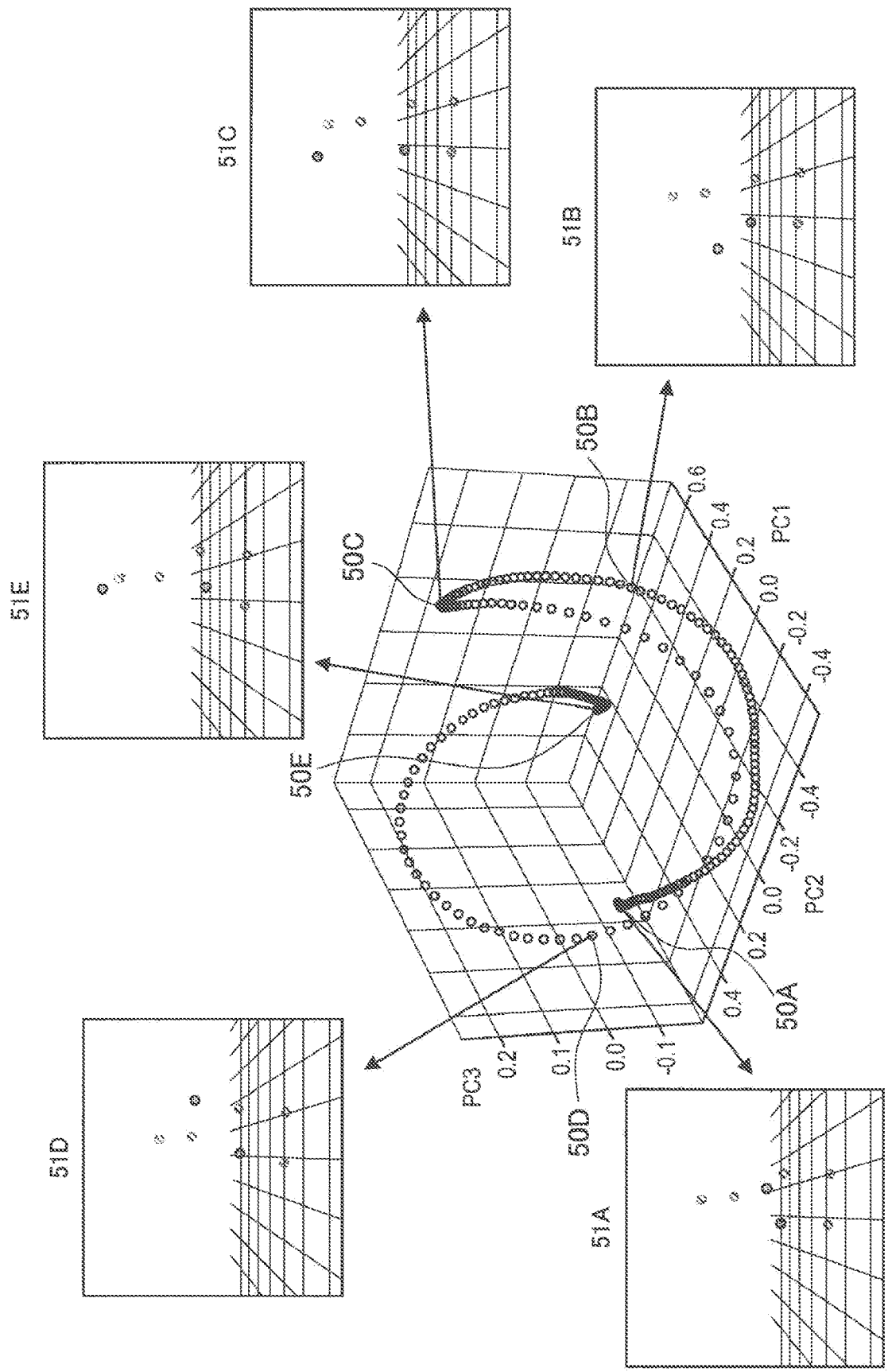
FIG. 8 is a diagram illustrating an example of a dimension-compressed operation model according to the embodiment.

FIG. 8 is a diagram illustrating an example of a dimension-compressed operation model according to the present embodiment. FIG. 8 illustrates an example of an operation model obtained by compressing 21-dimensional information related to seven regions other than the club head of the iron, into three dimension including a first principal component (PC1), a second principal component (PC2), and a third principal component (PC3). The club head of the iron is excluded for enhancing prediction accuracy. Each plot in a space of the dimension-compressed operation model corresponds to an attitude of a person at each timing in the golf swing. For example, plots 50A to 50F respectively correspond to attitudes 51A to 51F.

Subsequently, a prediction algorithm that uses a dimension-compressed operation model will be described with reference to FIG. 9.

Figure 9:
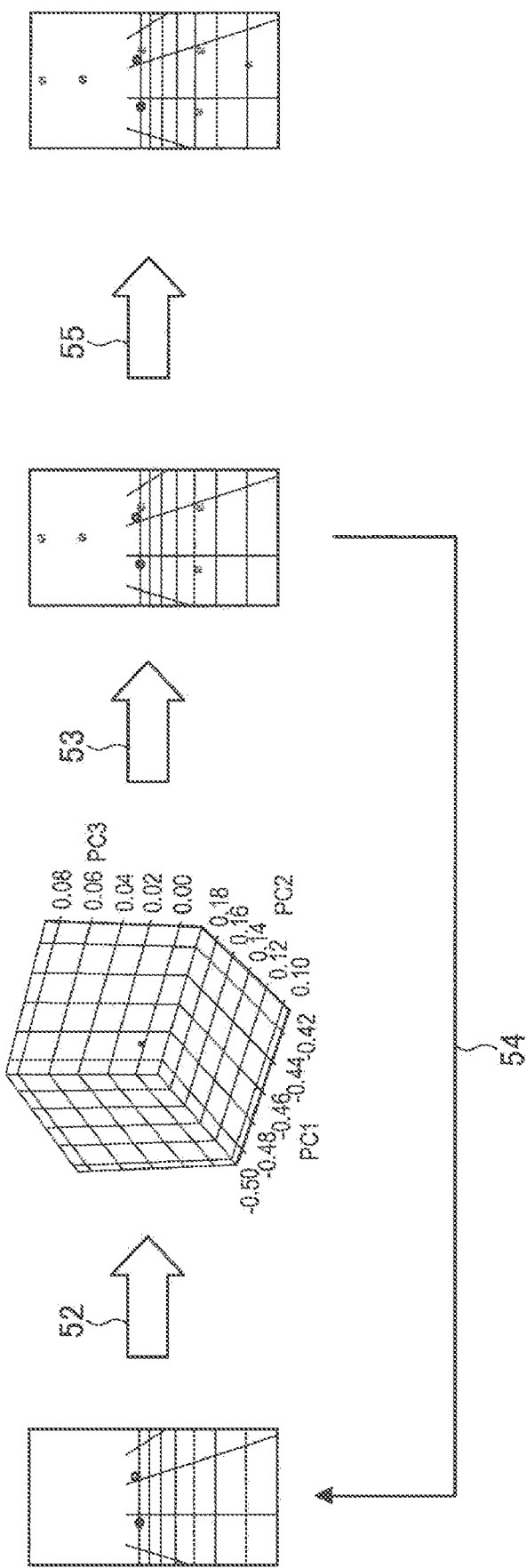
FIG. 9 is a diagram for describing an example of a prediction algorithm according to the embodiment.

FIG. 9 is a diagram for describing an example of a prediction algorithm according to the present embodiment. As illustrated in FIG. 9, the information processing apparatus 30 calculates position information pieces of first points (the right knee and the hand). Subsequently, the information processing apparatus 30 searches for a point on a compression space in which the position information pieces of the first points are to be reproduced, by a steepest descent method (reference numeral 52), and calculates position information pieces of the first points and second points, from the retrieved one point, by PCA inverse mapping (reference numeral 53). The information processing apparatus 30 repeatedly performs these calculations until a difference between the position information pieces of the first points that are obtainable before and after the search falls below a threshold value (reference numeral 54). After that, the information processing apparatus 30 predicts, by linear regression, position information of the club head of the iron on the basis of the position information pieces of the first points and the second points (reference numeral 55).

By performing the above-described prediction processing at each timing of the swing, the information processing apparatus 30 can visualize the entire operation in which the user swings the iron, as illustrated in FIG. 6.

Note that the information processing apparatus 30 may use Gaussian Process Latent Variable Models (GPLVM), for example, as an alternative dimension compression method of the PCA. The GPLVM is a nonlinear compression method, and is suitable for predicting a more complicated operation although costs of learning and prediction are higher than those in the PCA.

(7) Information Output

The information processing apparatus 30 (e.g. the output control section 355) outputs output information indicating the calculated overall operation of the target object. The information output may be performed in real time concurrently with the operation of the user, or may be performed at an arbitrary timing after the measurement.

For example, the output information may be an image (a moving image or a still image) in which a virtual object corresponding to the target object performs an operation corresponding to the overall operation of the target object. For example, the output information may be an image indicating a time series variation of position information of each point of the user, as illustrated in FIG. 6. Additionally, the output information may be an image in which an avatar corresponding to the user performs an operation corresponding to an operation of the user. A User Interface (UI) example in this case will be described with reference to FIG. 10.

Figure 10:
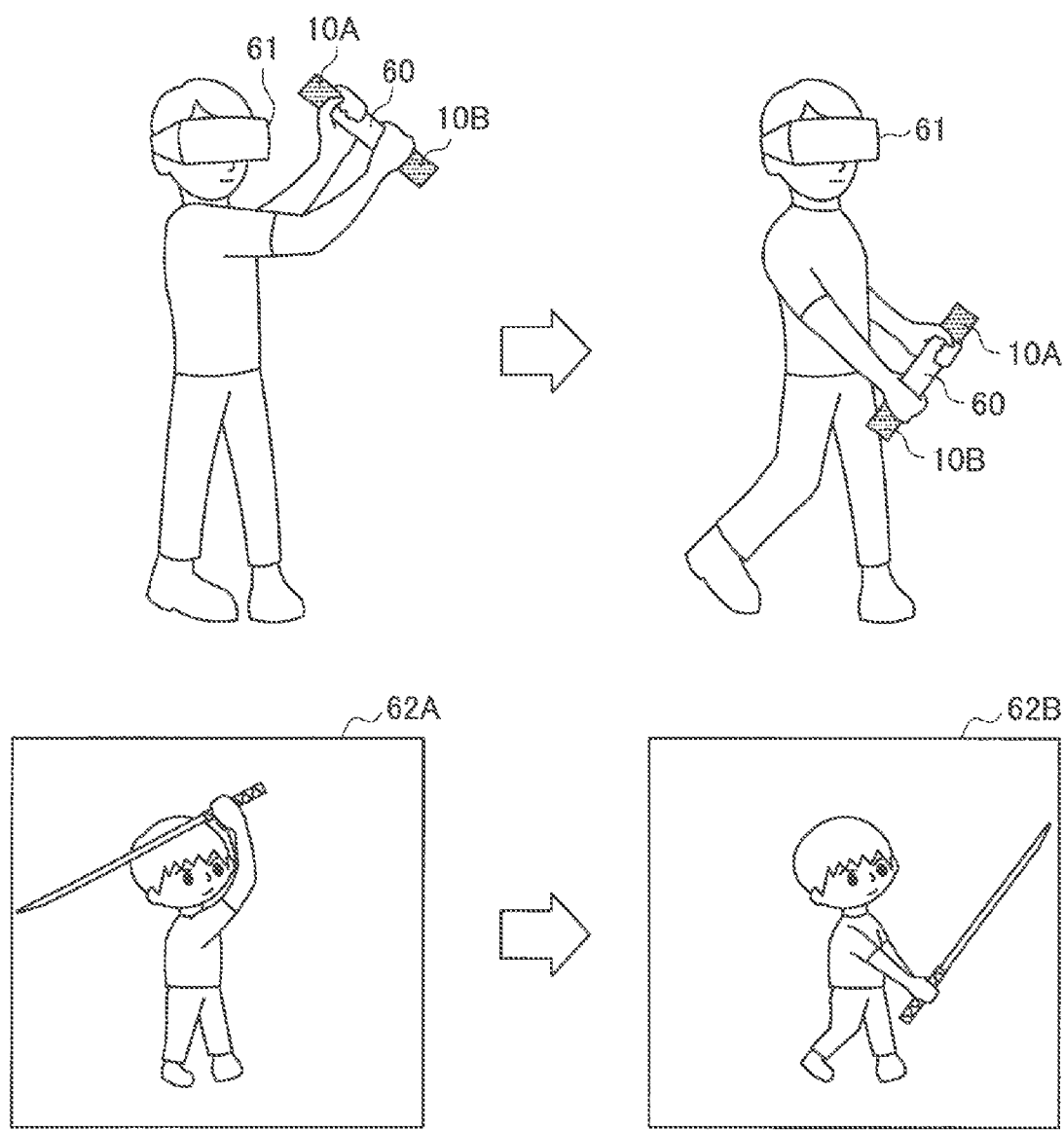
FIG. 10 is a diagram for describing an example of a UI according to the embodiment.

FIG. 10 is a diagram for describing an example of a UI according to the present embodiment. As illustrated in FIG. 10, the user holds a controller 60 for games that includes sensor devices 10A and 10B, and wears a virtual reality (VR) device 61. By varying a position or an attitude of the controller 60, the user manipulates an avatar displayed on the VR device 61. Specifically, the entire attitude of the user is calculated on the basis of calculation results of position information pieces of the sensor devices 10A and 10B, and a calculation result of the overall attitude is reflected on a move of the avatar. For example, as illustrated in FIG. 10, when the user holds up the controller 60 overhead, and then, swings down the controller 60, an image 62A in which the avatar holds up a sword overhead, and an image 62B in which the avatar swings down the sword are displayed on the VR device 61. Here, although the sensor devices 10 are not arranged on the feet of the user, a move of the feet can be reproduced in the avatar by the above-described prediction processing.

Additionally, the output information may be an instruction related to an attachment position of the sensor device 10. For example, the information processing apparatus 30 may output information instructing an optimum attachment position of the sensor device 10, on the basis of an analysis result of PCA. Table 1 described below indicates an example of a contribution ratio and a factor loading of each principal component in a swing operation of an iron.

TABLE 1

|  | Principal component | | |
|---|---|---|---|
|  | PC1 | PC2 | PC3 |
| Contribution ratio (cumulative) | 0.6584 (65.8%) | 0.2820 (94.0%) | 0.0500 (99.0%) |
| Factor loading | Hand (0.0918) | Hand (0.0296) | Hand (0.0059) |
|  | Right Knee (0.0237) | Right Knee (0.0154) | Right Knee (0.0041) |
|  | Waist (0.0152) | Left Knee (0.0129) | Left Knee (0.0025) |
|  | Right Foot (0.0080) | Waist (0.0054) | Waist (0.0014) |
|  | Left Knee (0.0072) | Right Foot (0.0043) | Right Foot (0.0014) |
|  | Neck (0.0070) | Neck (0.0037) | Neck (0.0012) |
|  | Left Foot (0.0010) | Left Foot (0.0005) | Left Foot (0.0003) |

As illustrated in Table 1 described above, a contribution ratio of a first principal component is 65.8%, a cumulative contribution ratio of the first principal component and a second principal component is 94%, and a cumulative contribution ratio of first to third principal components is 99%. In addition, in Table 1 described above, factors are listed in the order of larger factor loadings of each principal component. When the sensor devices 10 are attached to regions corresponding to factors having larger sums of factor loadings in the first to third principal components, it becomes possible to predict a swing operation using a smaller number of sensor devices 10. For example, according to Table 1 described above, in a case where the number of sensor devices 10 is two, the sensor devices 10 are desirably attached to the hand and the right knee. In view of the foregoing, the information processing apparatus 30 outputs information instructing the user that performs a swing operation, to attach the sensor devices 10 to the hand and the right knee.

<1.5. Flow of Processing>

Figure 11:
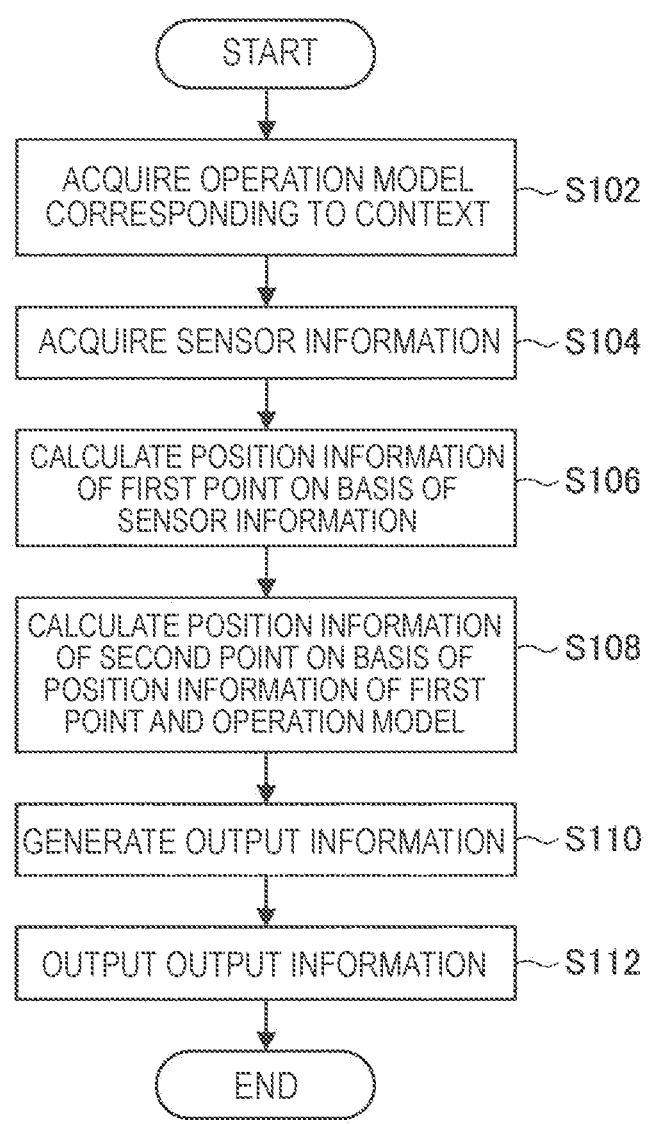
FIG. 11 is a flowchart illustrating an example of a flow of operation visualization processing executed in the information processing apparatus according to the embodiment.

Subsequently, an example of a flow of operation visualization processing executed in the information processing apparatus 30 according to the present embodiment will be described with reference to FIG. 11. FIG. 11 is a flowchart illustrating an example of a flow of operation visualization processing executed in the information processing apparatus 30 according to the present embodiment.

As illustrated in FIG. 11, first of all, the information processing apparatus 30 acquires an operation model corresponding to a context (step S102). For example, the information processing apparatus 30 acquires an operation model on the basis of a user manipulation, or acquires an operation model corresponding to an identified partial operation of the operations of a target object. Subsequently, the information processing apparatus 30 acquires sensor information measured and transmitted by the sensor device 10 (step S104). Subsequently, the information processing apparatus 30 calculates position information of a first point on the basis of the sensor information (step S106). Then, the information processing apparatus 30 calculates position information of a second point on the basis of the position information of the first point and the operation model (step S108). Next, the information processing apparatus 30 generates output information (step S110). For example, the information processing apparatus 30 generates an image on the basis of the position information of the first point and the position information of the second point, or generates information instructing an optimum attachment position of the sensor device 10, on the basis of an analysis result of PCA. Subsequently, the information processing apparatus 30 outputs the generated output information (step S112).

The processing ends through the above flow.

2. Second Embodiment

The present embodiment is a mode of visualizing an operation of a virtual object.

A system 1 according to the present embodiment includes an information processing apparatus 30. A configuration example of the information processing apparatus 30 according to the present embodiment will be described below with reference to FIG. 12.

<2.1. Configuration Example of Information Processing Apparatus>

Figure 12:
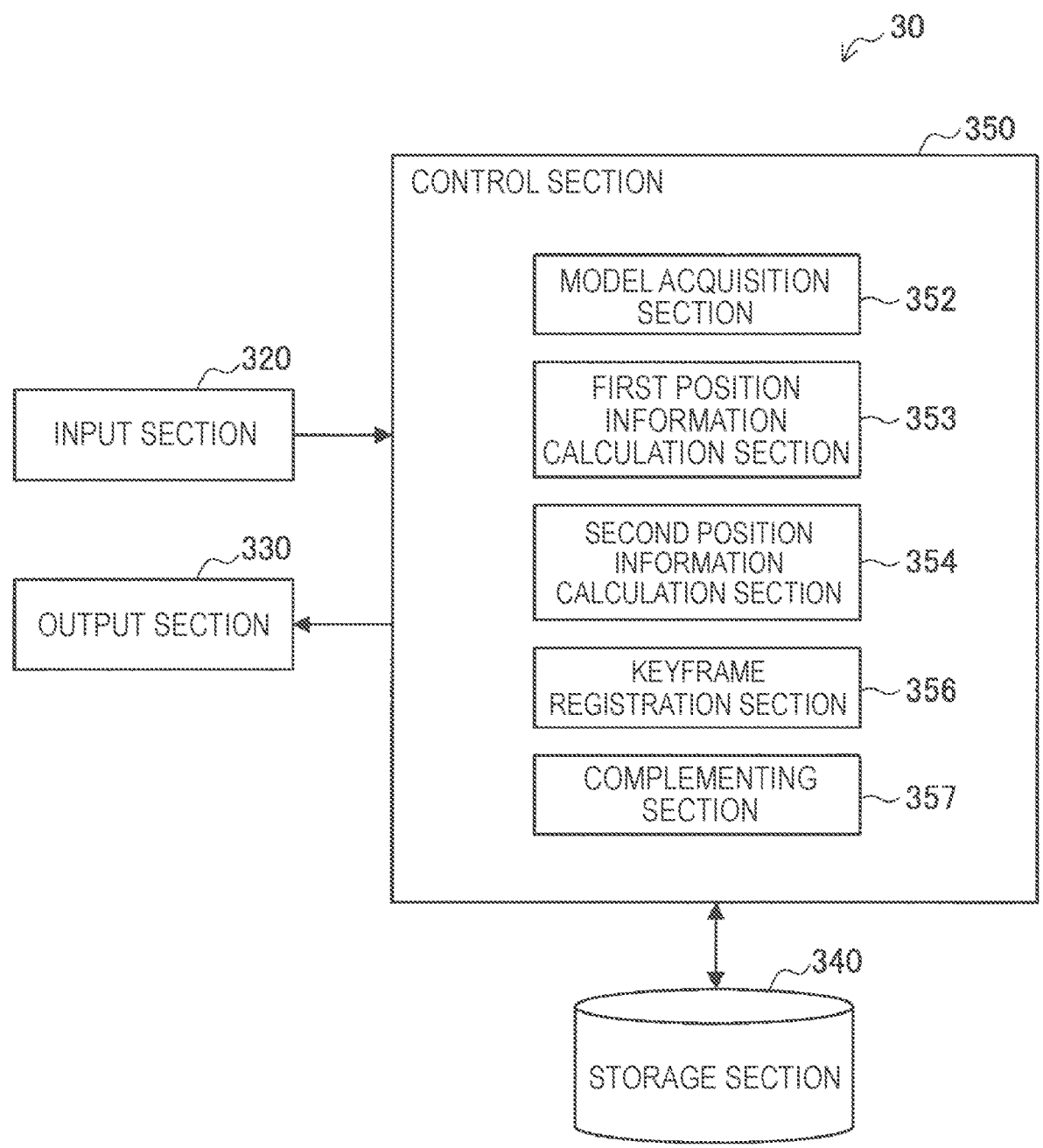
FIG. 12 is a block diagram illustrating an example of a configuration of an information processing apparatus according to a second embodiment.

FIG. 12 is a block diagram illustrating an example of a configuration of the information processing apparatus 30 according to the present embodiment. As illustrated in FIG. 12, the information processing apparatus 30 according to the present embodiment includes the input section 320, the output section 330, the storage section 340, and a control section 350. Note that, because the functions of the input section 320, the output section 330, and the storage section 340 are similar to those in the first embodiment, the description here will be omitted.

The control section 350 corresponds to a CPU, a DSP, or the like, and performs processing for providing various types of functions of the information processing apparatus 30. The control section 350 may be regarded as at least one electrical circuit formed so as to be able to execute functional units disclosed in FIG. 12. As illustrated in FIG. 12, the control section 350 includes the model acquisition section 352, the first position information calculation section 353, the second position information calculation section 354, a keyframe registration section 356, and a complementing section 357. Note that the control section 350 can further include structural elements other than these structural elements. In other words, the control section 350 can also perform operations other than operations of these structural elements. The operations of these structural elements will be described in detail later.

<2.2. Technical Feature>

(1) Target Object

In the present embodiment, a target object is a virtual object. In addition, position information in the present embodiment is a three-dimensional coordinate in a virtual space.

For example, the target object may include one or more virtual moving objects.

For example, the target object may include a virtual moving object having a plurality of joints. Then, an operation of the target object may include time series variations of position information pieces of the plurality of joints of the virtual moving object.

In the present embodiment, a target object to be visualized is assumed to be an avatar of a virtual human.

Hereinafter, a manipulator of the information processing apparatus 30 will also be referred to as a user.

In the present embodiment, among regions of a virtual object, a region manipulated by the user will also be referred to as a first point. In addition, among regions of a virtual object, a region not manipulated by the user will also be referred to as a second point.

(2) Calculation of Position Information that is Based on User Manipulation

The information processing apparatus 30 (e.g. the first position information calculation section 353) identifies a partial operation of the virtual object on the basis of manipulation information of the user with respect to the virtual object. Specifically, the information processing apparatus 30 calculates position information of the first point on the basis of manipulation information indicating a user manipulation instructing a partial operation of the virtual object For example, upon receiving a manipulation of moving one joint of an avatar by drag, the information processing apparatus 30 calculates position information of the moved joint on the basis of a drag amount and a drag direction.

(3) Calculation of Position Information that is Based on Operation Model

The information processing apparatus 30 (e.g. the second position information calculation section 354) calculates a time series variation of position information of another region of the target object that follows an operation pattern indicated by an operation model, and corresponds to a time series variation of position information of one or more manipulation target regions. In other words, the information processing apparatus 30 calculates a time series variation of position information of the second point that follows an operation pattern indicated by an operation model, and corresponds to a time series variation of position information of the first point. It thereby becomes possible for the information processing apparatus 30 to calculate an overall operation of the avatar that includes time series variations of the position information of the first point and the position information of the second point.

Note that the technical features related to an operation model, the selection of the operation model, and prediction algorithms are similar to those in the first embodiment except that the target object is a virtual object, and calculation of position information that is based on sensor information becomes calculation of position information that is based on manipulation information.

(4) Information Output

UI Example

Typically, the information processing apparatus 30 according to the present embodiment is used for production support for 3D animation. An example of a UI for production support for 3D animation will be described with reference to FIG. 13.

Figure 13:
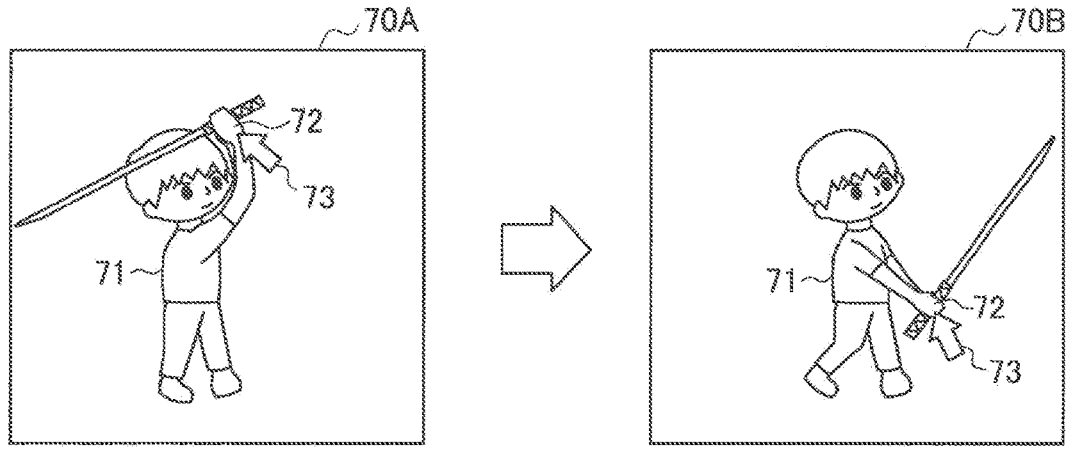
FIG. 13 is a diagram illustrating an example of a UI according to the embodiment.

FIG. 13 is a diagram illustrating an example of a UI according to the present embodiment. As illustrated in FIG. 13, an avatar 71 is displayed on a production screen 70A. On the production screen 70A, the user selects and drags a right hand 72 of the avatar 71 by a pointer 73. As a result, as in a production screen 70B, not only the dragged right hand 72 (i.e. the first point), but also a left hand, both feet, and the like (i.e. second points) move in accordance with the move of the right hand 72. In this manner, the user can cause the avatar 71 to perform a natural operation, only by designating a move of a partial region, without finely designating a whole-body move of the avatar 71 for each region. Accordingly, load on production of 3D animation can be reduced.

Generation of Animation

The information processing apparatus 30 generates animation using a keyframe method, for example. The keyframe method is a technology of generating a moving image by arranging keyframes at every several frames, and complementing between the keyframes.

For example, the information processing apparatus 30 (e.g. the keyframe registration section 356) registers a keyframe of animation. For example, the information processing apparatus 30 registers, as a keyframe, an attitude of the avatar 71 manipulated by the user on a production screen as illustrated in FIG. 13.

Subsequently, the information processing apparatus 30 (e.g. the complementing section 357) generates animation by complementing between keyframes.

<2.3. Flow of Processing>

Figure 14:
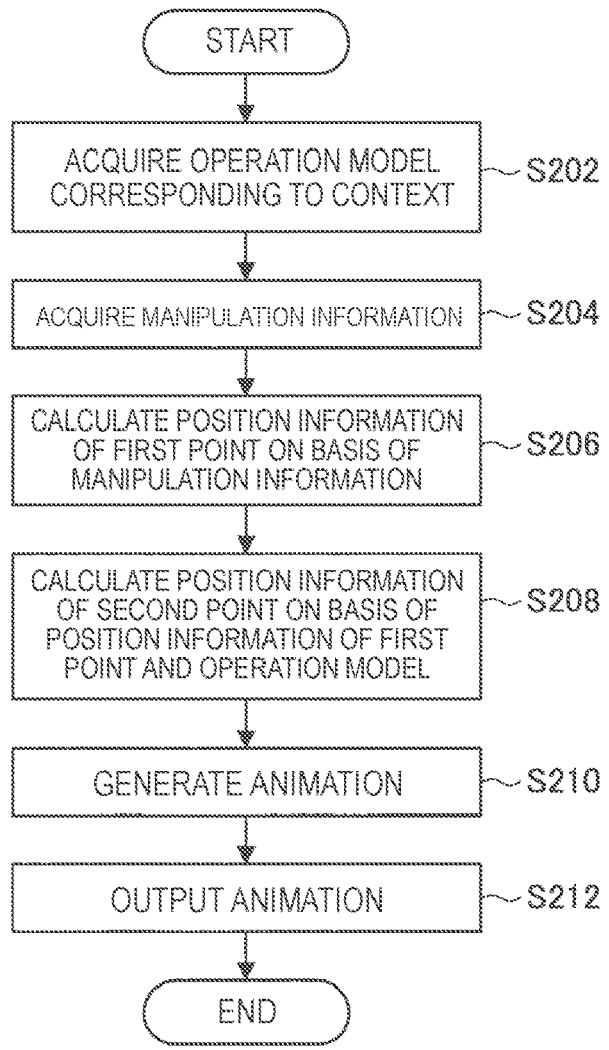
FIG. 14 is a flowchart illustrating an example of a flow of operation visualization processing executed in the information processing apparatus according to the embodiment.

Subsequently, an example of a flow of operation visualization processing executed in the information processing apparatus 30 according to the present embodiment will be described with reference to FIG. 14. FIG. 14 is a flowchart illustrating an example of a flow of operation visualization processing executed in the information processing apparatus 30 according to the present embodiment.

As illustrated in FIG. 14, first of all, the information processing apparatus 30 acquires an operation model corresponding to a context (step S202). For example, the information processing apparatus 30 acquires an operation model on the basis of a user manipulation. Subsequently, the information processing apparatus 30 acquires manipulation information indicating a user manipulation instructing a partial operation of the virtual object (step S204). Next, the information processing apparatus 30 calculates position information of the first point on the basis of the manipulation information (step S206). Then, the information processing apparatus 30 calculates position information of the second point on the basis of the position information of the first point and the operation model (step S208). Next, the information processing apparatus 30 generates animation (step S210). For example, the information processing apparatus 30 generates animation by registering a group of keyframes, and complementing between the keyframes. Subsequently, the information processing apparatus 30 outputs the generated animation (step S212).

The processing ends through the above flow.

3. Hardware Configuration Example

Figure 15:
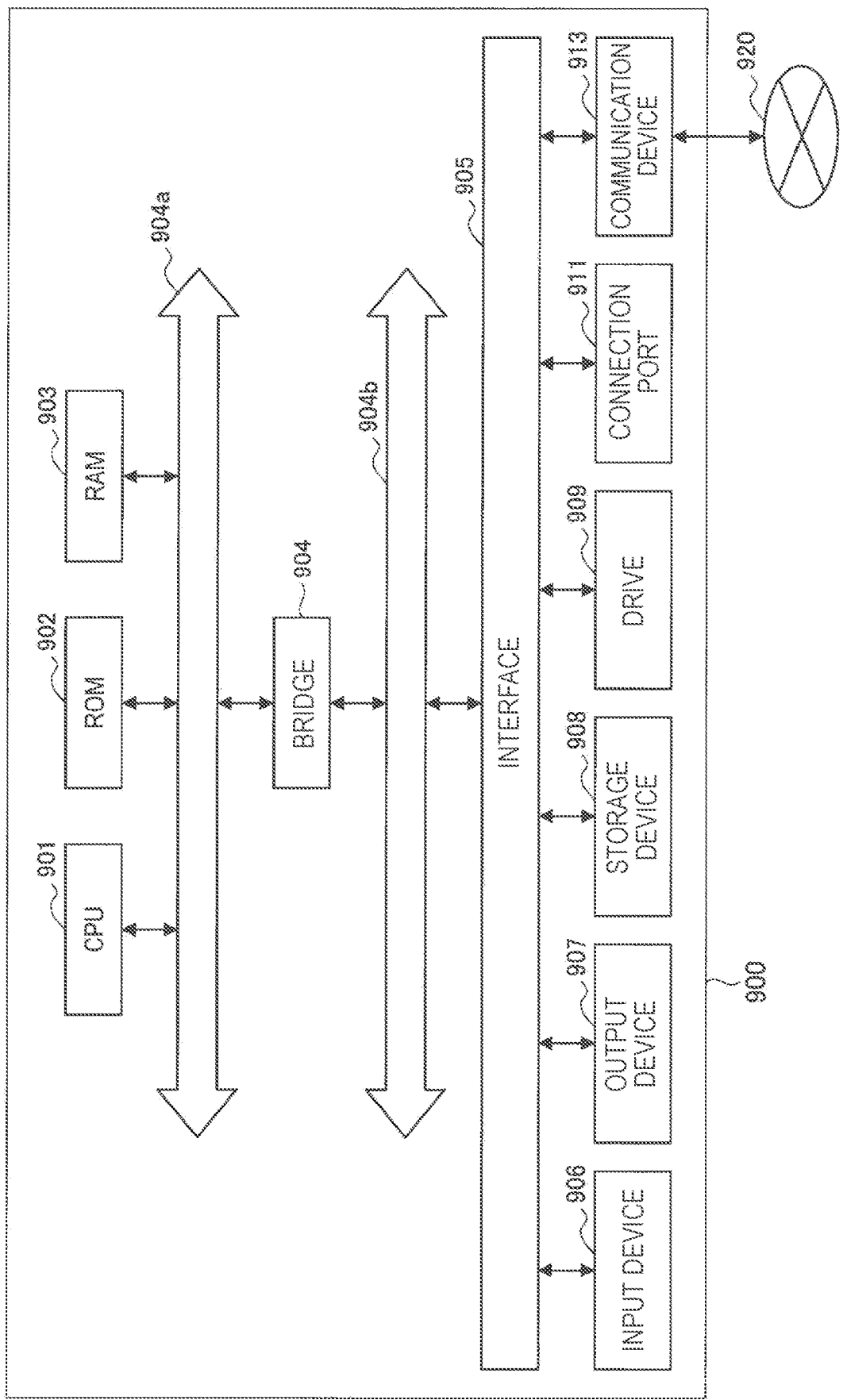
FIG. 15 is a block diagram illustrating an example of the hardware configuration of the information processing apparatus according to each of the embodiments.

Finally, a hardware configuration of an information processing apparatus according to each of the embodiments will be described with reference to FIG. 15. FIG. 15 is a block diagram illustrating an example of the hardware configuration of the information processing apparatus according to each of the embodiments. Meanwhile, the information processing apparatus 900 illustrated in FIG. 15 may realize the information processing apparatus 30 illustrated in each of FIG. 3 or FIG. 12, for example. Information processing by the information processing apparatus 30 according to each of the embodiments is realized according to cooperation between software and hardware described below.

As illustrated in FIG. 15, the information processing apparatus 900 includes a central processing unit (CPU) 901, a read only memory (ROM) 902, a random access memory (RAM) 903 and a host bus 904a. In addition, the information processing apparatus 900 includes a bridge 904, an external bus 904b, an interface 905, an input device 906, an output device 907, a storage device 908, a drive 909, a connection port 911 and a communication device 913. The information processing apparatus 900 may include a processing circuit such as a DSP or an ASIC instead of the CPU 901 or along therewith.

The CPU 901 functions as an arithmetic processing device and a control device and controls the overall operation in the information processing apparatus 900 according to various programs. Further, the CPU 901 may be a microprocessor. The ROM 902 stores programs, operation parameters and the like used by the CPU 901. The RAM 903 temporarily stores programs used in execution of the CPU 901, parameters appropriately changed in the execution, and the like. The CPU 901 may form the control section 350 illustrated in FIG. 3 or FIG. 12, for example.

The CPU 901, the ROM 902 and the RAM 903 are connected by the host bus 904a including a CPU bus and the like. The host bus 904a is connected with the external bus 904b such as a peripheral component interconnect/interface (PCI) bus via the bridge 904. Further, the host bus 904a, the bridge 904 and the external bus 904b are not necessarily separately configured and such functions may be mounted in a single bus.

The input device 906 is realized by a device through which a user inputs information, such as a mouse, a keyboard, a touch panel, a button, a microphone, a switch, and a lever. In addition, the input device 906 may be a remote control device using infrared ray or other electric waves or external connection equipment such as a cellular phone or a PDA corresponding to operation of the information processing apparatus 900, for example. Furthermore, the input device 906 may include an input control circuit or the like which generates an input signal on the basis of information input by the user using the aforementioned input means and outputs the input signal to the CPU 901, for example. The user of the information processing apparatus 900 may input various types of data or order a processing operation for the information processing apparatus 900 by operating the input device 906. The input device 906 may form the input section 320 illustrated in FIG. 3 or FIG. 12, for example.

In addition to the above, the input device 906 can be formed by a device that detects information related to the user. For example, the input device 906 can include various sensors such as an image sensor (a camera, for example), a depth sensor (a stereo camera, for example), an acceleration sensor, a gyro sensor, a geomagnetic sensor, an optical sensor, a sound sensor, a distance measurement sensor, and a force sensor. Also, the input device 906 may acquire information related to the state of the information processing apparatus 900 itself such as the posture and the moving velocity of the information processing apparatus 900 and information related to a surrounding environment of the information processing apparatus 900 such as brightness or noise around the information processing apparatus 900. Also, the input device 906 may include a GNSS module that receives a GNSS signal (a GPS signal from a global positioning system (GPS) satellite, for example) from a global navigation satellite system (GNSS) satellite and measures position information including the latitude, the longitude, and the altitude of the device. In addition, the input device 906 may detect the position through Wi-Fi (registered trademark), transmission and reception to and from a mobile phone, a PHS, a smartphone, or the like, near-field communication, or the like, in relation to the position information.

The output device 907 is formed by a device that may visually or aurally notify the user of acquired information. As such devices, there is a display device such as a CRT display device, a liquid crystal display device, a plasma display device, an EL display device, a laser projector, an LED projector or a lamp, a sound output device such as a speaker and a headphone, a printer device and the like. The output device 907 outputs results acquired through various processes performed by the information processing apparatus 900, for example. Specifically, the display device visually displays results acquired through various processes performed by the information processing apparatus 900 in various forms such as text, images, tables and graphs. On the other hand, the sound output device converts audio signals including reproduced sound data, audio data and the like into analog signals and aurally outputs the analog signals. The aforementioned display device and the aforementioned sound output device may form the output section 330 illustrated in FIG. 3 or FIG. 12, for example.

The storage device 908 is a device for data storage, formed as an example of a storage section of the information processing apparatus 900. For example, the storage device 908 is realized by a magnetic storage device such as an HDD, a semiconductor storage device, an optical storage device, a magneto-optical storage device or the like. The storage device 908 may include a storage medium, a recording device for recording data on the storage medium, a reading device for reading data from the storage medium, a deletion device for deleting data recorded on the storage medium and the like. The storage device 908 stores programs and various types of data executed by the CPU 901, various types of data acquired from the outside and the like. The storage device 908 may form the storage section 340 illustrated in FIG. 3 or FIG. 12, for example.

The drive 909 is a reader/writer for storage media and is included in or externally attached to the information processing apparatus 900. The drive 909 reads information recorded on a removable storage medium such as a magnetic disc, an optical disc, a magneto-optical disc or a semiconductor memory mounted thereon and outputs the information to the RAM 903. In addition, the drive 909 can write information on the removable storage medium.

The connection port 911 is an interface connected with external equipment and is a connector to the external equipment through which data may be transmitted through a universal serial bus (USB) and the like, for example.

The communication device 913 is a communication interface formed by a communication device for connection to a network 920 or the like, for example. The communication device 913 is a communication card or the like for a wired or wireless local area network (LAN), long term evolution (LTE), Bluetooth (registered trademark) or wireless USB (WUSB), for example. In addition, the communication device 913 may be a router for optical communication, a router for asymmetric digital subscriber line (ADSL), various communication modems or the like. For example, the communication device 913 may transmit/receive signals and the like to/from the Internet and other communication apparatuses according to a predetermined protocol, for example, TCP/IP or the like. The communication device 913 may form the communication section 310 illustrated in FIG. 3, for example.

Further, the network 920 is a wired or wireless transmission path of information transmitted from devices connected to the network 920. For example, the network 920 may include a public circuit network such as the Internet, a telephone circuit network or a satellite communication network, various local area networks (LANs) including Ethernet (registered trademark), a wide area network (WAN) and the like. In addition, the network 920 may include a dedicated circuit network such as an internet protocol-virtual private network (IP-VPN).

Hereinbefore, an example of a hardware configuration capable of realizing the functions of the information processing apparatus 900 according to each of the embodiments is shown. The respective components may be implemented using universal members, or may be implemented by hardware specific to the functions of the respective components. Accordingly, according to a technical level at the time when each of the embodiments are executed, it is possible to appropriately change hardware configurations to be used.

In addition, a computer program for realizing each of the functions of the information processing apparatus 900 according to each of the embodiments as described above may be created, and may be mounted in a PC or the like. Furthermore, a computer-readable recording medium on which such a computer program is stored may be provided. The recording medium is a magnetic disc, an optical disc, a magneto-optical disc, a flash memory, or the like, for example. Further, the computer program may be delivered through a network, for example, without using the recording medium.

4. Conclusion

An embodiment of the present disclosure has been described in detail above with reference to FIG. 1 to FIG. 15. As described above, the information processing apparatus 30 according to the present embodiment acquires an operation model indicating an operation pattern related to a target object, and calculates an overall operation from an identified partial operation of operations of the target object, with reference to the acquired operation model. In the first embodiment, it thereby becomes possible to predict operations of the overall regions of the target object, by sensor information pieces obtained from the sensor devices 10 attached to partial regions of the target object. In addition, in the second embodiment, it becomes possible to generate animation in which the overall regions of the target object are operated, by a user manipulation of operating a partial region of the target object. In this manner, the information processing apparatus 30 can visualize an operation of a target object from a smaller amount of information. Note that operation information may be output by specifying, as a target object, a specific section such as an arm, a foot, an upper body, or a lower body of the user. In other words, in this specification, a "target object" is not limited to a target object that is physically or virtually independent.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, the first embodiment and the second embodiment of the present disclosure can be appropriately combined. For example, animation indicating a user operation may be generated by registering keyframes on the basis of operations of the user at respective timings, and complementing between the keyframes.

For example, devices described in this specification may be implemented as independent devices, or a part or all thereof may be implemented as separate devices. For example, in the functional configuration example of the information processing apparatus 30 that is illustrated in FIG. 3 or 12, the storage section 340 and/or the control section 350 may be included in a device such as a server that is connected with the input section 320 and the output section 330 via a network or the like. In addition, the sensor device 10 and the information processing apparatus 30 may be integrally formed.

Note that it is not necessary for the processing described in this specification with reference to the flowchart and the sequence diagram to be executed in the order shown in the flowchart. Some processing steps may be performed in parallel. Further, some of additional steps can be adopted, or some processing steps can be omitted.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An information processing apparatus including:
an acquisition section configured to acquire an operation model indicating an operation pattern related to a target object;
a calculation section configured to calculate an overall operation including an identified partial operation of operations of the target object, with reference to the operation model acquired by the acquisition section; and
an output control section configured to output output information indicating the overall operation of the target object that has been calculated by the calculation section.

(2)

The information processing apparatus according to (1), in which the acquisition section acquires the operation model corresponding to a context of the target object.

(3)

The information processing apparatus according to (2), in which the acquisition section acquires the operation model on a basis of a user manipulation.

(4)

The information processing apparatus according to (2), in which the acquisition section acquires the operation model corresponding to an identified partial operation of operations of the target object.

(5)

The information processing apparatus according to (3) or (4), in which the target object includes a user,
the operation model includes a first operation model and a second operation model, and
the acquisition section recognizes the context on a basis of a partial operation of the user that has been identified by sensor information measured by a sensor device arranged on the user, and automatically acquires one of the first operation model and the second operation model in accordance with the recognized context.

(6)

The information processing apparatus according to any one of (1) to (5), in which the output information includes an image in which a virtual object corresponding to the target object performs an operation corresponding to the overall operation of the target object.

(7)

The information processing apparatus according to (6), in which the target object includes a user, and the output information is displayed by a virtual reality (VR) device worn by the user.

(8)

The information processing apparatus according to any one of (1) to (7), in which the target object is a real object, and the calculation section identifies, on a basis of sensor information measured by a sensor device arranged on the target object, a time series variation of position information of the sensor device.

(9)

The information processing apparatus according to (8), in which the calculation section calculates a time series variation of position information of another region of the target object that follows the operation pattern indicated by the operation model, and corresponds to a time series variation of position information of the one or more sensor devices.

(10)

The information processing apparatus according to (8) or (9), in which the sensor device is arranged at a joint corresponding to a context, among a plurality of predefined joints.

(11)

The information processing apparatus according to (10), in which the sensor devices are arranged at two locations including a hand and a knee, in a case where the context is a swing operation of a golf club.

(12)

The information processing apparatus according to any one of (8) to (11), in which the sensor device includes an inertial sensor.

(13)

The information processing apparatus according to any one of (8) to (12), in which the sensor device is removably attached to a sensor attachment tool for fixing the sensor device on the target object.

(14)

The information processing apparatus according to (1), in which the target object includes a user and an object manipulated by the user.

(15)

The information processing apparatus according to (14), in which the calculation section calculates, on a basis of an identified operation of a user, an operation of an object manipulated by the user, with reference to the operation model.

(16)

The information processing apparatus according to (15), in which the calculation section calculates, on a basis of an identified swing operation of a user, an operation of a golf club swung by the user, with reference to the operation model related to a swing operation of a golf club.

(17)

The information processing apparatus according to any one of (1) to (7), in which the target object is a virtual object, and the calculation section identifies a partial operation of the virtual object on a basis of manipulation information of a user with respect to the virtual object.

(18)

The information processing apparatus according to any one of (1) to (17), in which the target object includes a moving object having a plurality of joints, and an operation of the target object includes time series variations of position information of the plurality of joints of the moving object.

(19)

An information processing method including:

acquiring an operation model indicating an operation pattern related to a target object;

calculating, by a processor, an overall operation including an identified partial operation of operations of the target object, with reference to the acquired operation model; and outputting output information indicating the calculated overall operation of the target object.

(20)

A storage medium storing a program for causing a computer to function as:

an acquisition section configured to acquire an operation model indicating an operation pattern related to a target object;

a calculation section configured to calculate an overall operation including an identified partial operation of operations of the target object, with reference to the operation model acquired by the acquisition section; and an output control section configured to output output information indicating the overall operation of the target object that has been calculated by the calculation section.

REFERENCE SIGNS LIST

1 system
10 sensor device
110 inertial sensor
120 communication section
130 storage section
140 control section
20 sensor attachment apparatus
21 sensor attachment tool
30 information processing apparatus
310 communication section
320 input section
330 output section
340 storage section
350 control section
351 model learning section
352 model acquisition section
353 first position information calculation section
354 second position information calculation section
355 output control section
356 keyframe registration section
357 complementing section

The invention claimed is:

1. An information processing apparatus, comprising:
 a memory configured to store a plurality of operation models; and
 circuitry configured to:
  acquire sensor information associated with a target object, wherein
   the acquired sensor information includes a first plurality of position information pieces,
   each position information piece of the first plurality of position information pieces corresponds to a respective sensor device of a plurality of sensor devices attached to a first plurality of regions on the target object, and
   the target object includes a user;
  determine a partial operation of the user based on the acquired sensor information;

determine a type of the partial operation of the target object based on the determined partial operation;
acquire a specific operation model of the stored plurality of operation models, wherein
the specific operation model is associated with the type of the partial operation of the target object,
the specific operation model corresponds to the determined partial operation, and
the specific operation model indicates an operation pattern associated with the target object;
predict a second plurality of position information pieces of a second plurality of regions on the target object for each time point of the partial operation, wherein
the second plurality of position information pieces of the second plurality of regions on the target object is predicted based on the sensor information related to the first plurality of regions and the acquired specific operation model,
the second plurality of regions is different from the first plurality of regions, and
the second plurality of regions are regions on the target object to which no sensor devices are attached;
determine an overall operation of the target object that includes the first plurality of regions and the second plurality of regions; and
output operation information that indicates the overall operation of the target object.

2. The information processing apparatus according to claim 1, wherein the circuitry is further configured to acquire the specific operation model based on a user manipulation.

3. The information processing apparatus according to claim 2, wherein
the specific operation model comprises a first operation model and a second operation model,
and the circuitry is further configured to
acquire at least one of the first operation model or the second operation model based on the determined type of the partial operation of the target object.

4. The information processing apparatus according to claim 1, wherein
the operation information further comprises an image of a virtual object, and
the virtual object corresponds to the target object.

5. The information processing apparatus according to claim 4, wherein
the operation information is displayed by a virtual reality (VR) device wearable by the user.

6. The information processing apparatus according to claim 1, wherein
the target object is a real object,
the circuitry is further configured to calculate a time series variation of each position information piece of the first plurality of position information pieces, and
the time series variation of each position information piece of the first plurality of position information pieces is calculated based on the sensor information.

7. The information processing apparatus according to claim 6, wherein
the circuitry is further configured to calculate a time series variation of each position information piece of the second plurality of position information pieces, and
the time series variation of each position information piece of the second plurality of position information pieces is associated with the time series variation of each position information piece of the first plurality of position information pieces.

8. The information processing apparatus according to claim 1, wherein
a sensor device of the plurality of sensor devices is at a joint of a plurality of joints, and
the plurality of joints is associated with the type of the partial operation of the target object.

9. The information processing apparatus according to claim 8, wherein
the sensor device is at one of two locations,
the two locations are a hand of the user and a knee of the user, and
the type of the partial operation of the target object is a swing operation of a golf club.

10. The information processing apparatus according to claim 1, wherein a sensor device of the plurality of sensor devices comprises an inertial sensor.

11. The information processing apparatus according to claim 1, wherein
a sensor device of the plurality of sensor devices is removably attached to a sensor attachment tool.

12. The information processing apparatus according to claim 1, wherein the target object further includes an object manipulated by the user.

13. The information processing apparatus according to claim 12, wherein
the circuitry is further configured to determine an operation of the object manipulated by the user, and
the operation of the object manipulated by the user is determined based on the partial operation and the specific operation model.

14. The information processing apparatus according to claim 13, wherein
the specific operation model corresponds to a swing operation of a golf club, and
the circuitry is further configured to determine an operation of the golf club swung by the user based on the specific operation model.

15. The information processing apparatus according to claim 1, wherein
the target object is a virtual object,
the circuitry is further configured to determine the partial operation of the virtual object based on manipulation information, and
the manipulation information is associated with manipulation of the virtual object by the user.

16. The information processing apparatus according to claim 1, wherein
the target object is a moving object having a plurality of joints, and
the operation of the target object includes time series variations of position information of the plurality of joints of the moving object.

17. An information processing method, comprising:
storing, in a memory, a plurality of operation models;
acquiring sensor information associated with a target object, wherein
the acquired sensor information includes a first plurality of position information pieces,
each position information piece of the first plurality of position information pieces corresponds to a respective sensor device of a plurality of sensor devices attached to a first plurality of regions on the target object, and the target object includes a user;
determining a partial operation of the user based on the acquired sensor information;
determining a type of the partial operation of the target object based on the determined partial operation;
acquiring a specific operation model of the stored plurality of operation models, wherein
  the specific operation model is associated with the type of the partial operation of the target object,
  the specific operation model corresponds to the determined partial operation, and
  the specific operation model indicates an operation pattern associated with the target object;
predicting a second plurality of position information pieces of a second plurality of regions on the target object for each time point of the partial operation, wherein
  the second plurality of position information pieces of the second plurality of regions on the target object is predicted based on the sensor information related to the first plurality of regions and the acquired specific operation model,
  the second plurality of regions is different from the first plurality of regions, and
  the second plurality of regions are regions on the target object to which no sensor devices are attached;
determining an overall operation of the target object that includes the first plurality of regions and the second plurality of regions; and
outputting operation information that indicates the overall operation of the target object.

18. A non-transitory computer-readable medium having stored thereon, computer executable-instructions that, when executed by a processor, cause the processor to execute operations, the operations comprising:
storing, in a memory, a plurality of operation models;
acquiring sensor information associated with a target object, wherein
  the acquired sensor information includes a first plurality of position information pieces,
  each position information piece of the first plurality of position information pieces corresponds to a respective sensor device of a plurality of sensor devices attached to a first plurality of regions on the target object, and
  the target object includes a user;
determining a partial operation of the user based on the acquired sensor information;
determining a type of the partial operation the target object based on the determined partial operation;
acquiring a specific operation model of the stored plurality of operation models, wherein
  the specific operation model is associated with the type of the partial operation of the target object,
  the specific operation model corresponds to the determined partial operation, and
  the specific operation model indicates an operation pattern associated with the target object;
predicting a second plurality of position information pieces of a second plurality of regions on the target object for each time point of the partial operation, wherein
  the second plurality of position information pieces of the second plurality of regions on the target object is predicted based on the sensor information related to the first plurality of regions and the acquired specific operation model,
  the second plurality of regions is different from the first plurality of regions, and
  the second plurality of regions are regions on the target object to which no sensor devices are attached;
determining an overall operation of the target object that includes the first plurality of regions and the second plurality of regions; and
outputting operation information that indicates the overall operation of the target object.

* * * * *